(12) United States Patent
Ciciliato et al.

(10) Patent No.: US 6,586,393 B2
(45) Date of Patent: Jul. 1, 2003

(54) ANTIBIOTICS GE 23077, PHARMACEUTICALLY ACCEPTABLE SALTS AND COMPOSITIONS, AND USE THEREOF

(75) Inventors: Ismaela Ciciliato, Busto Arsizio (IT); Emiliana Corti, Rovellasca (IT); Edoardo Giacomo Sarubbi, Fontenay-Sous-Bois (FR); Stefania Stefanelli, Legnano (IT); Nicoletta Montanini, Malnate (IT); Flavia Marinelli, Milan (IT); Michael Kurz, Hofheim (DE); Enrico Selva, Gropello Cairoli (IT)

(73) Assignee: Biosearch Italia S.p.A., Milan (IT)

( * ) Notice: Subject to any disclaimer, the term of this patent is extended or adjusted under 35 U.S.C. 154(b) by 0 days.

(21) Appl. No.: 09/986,540

(22) Filed: Nov. 9, 2001

(65) Prior Publication Data

US 2002/0115597 A1 Aug. 22, 2002

(30) Foreign Application Priority Data

Dec. 4, 2000 (EP) .............................................. 00126618

(51) Int. Cl.$^7$ ........................ A61K 38/00; A61K 31/33; A61K 35/00

(52) U.S. Cl. ............................. 514/9; 424/115; 514/10; 514/451; 435/71.3; 435/169; 435/252.1; 530/317

(58) Field of Search .............................. 514/9, 10, 451; 424/115; 435/71.3, 252.1, 169; 530/317

(56) References Cited

U.S. PATENT DOCUMENTS

| | | | | |
|---|---|---|---|---|
| 4,328,211 A | * | 5/1982 | Sugawara et al. | .......... 424/115 |
| 4,876,273 A | * | 10/1989 | Hamill et al. | ................ 514/451 |
| 5,534,420 A | * | 7/1996 | Debono et al. | ............ 435/71.3 |
| 5,567,676 A | * | 10/1996 | Selva et al. | ................. 424/115 |

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

The invention relates to an antibiotic substance of microbial origin, arbitrarily denominated GE23077 complex and the individual factors which constitute it, a mixture of said factors in any proportion, the pharmaceutically acceptable salts and compositions thereof, and their use as an antibacterial agent having a selective inhibitory activity against *E. coli* RNA polymerase.

17 Claims, 7 Drawing Sheets

Infrared spectrum of antibiotic GE23077 complex in nujol mull

FIG. 3  $^1$H-NMR spectrum of antibiotic GE23077 complex in DMSO-$d_6$

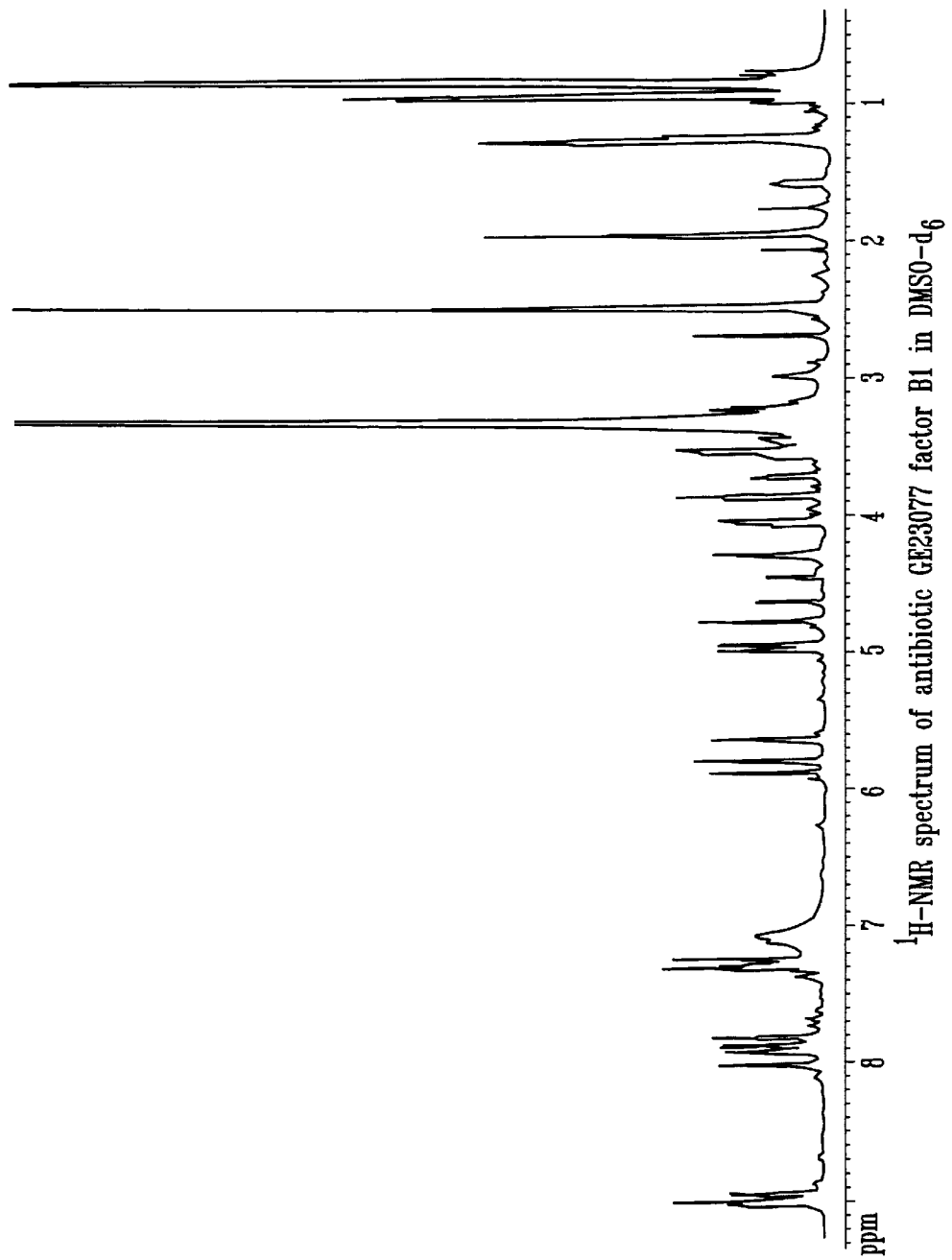

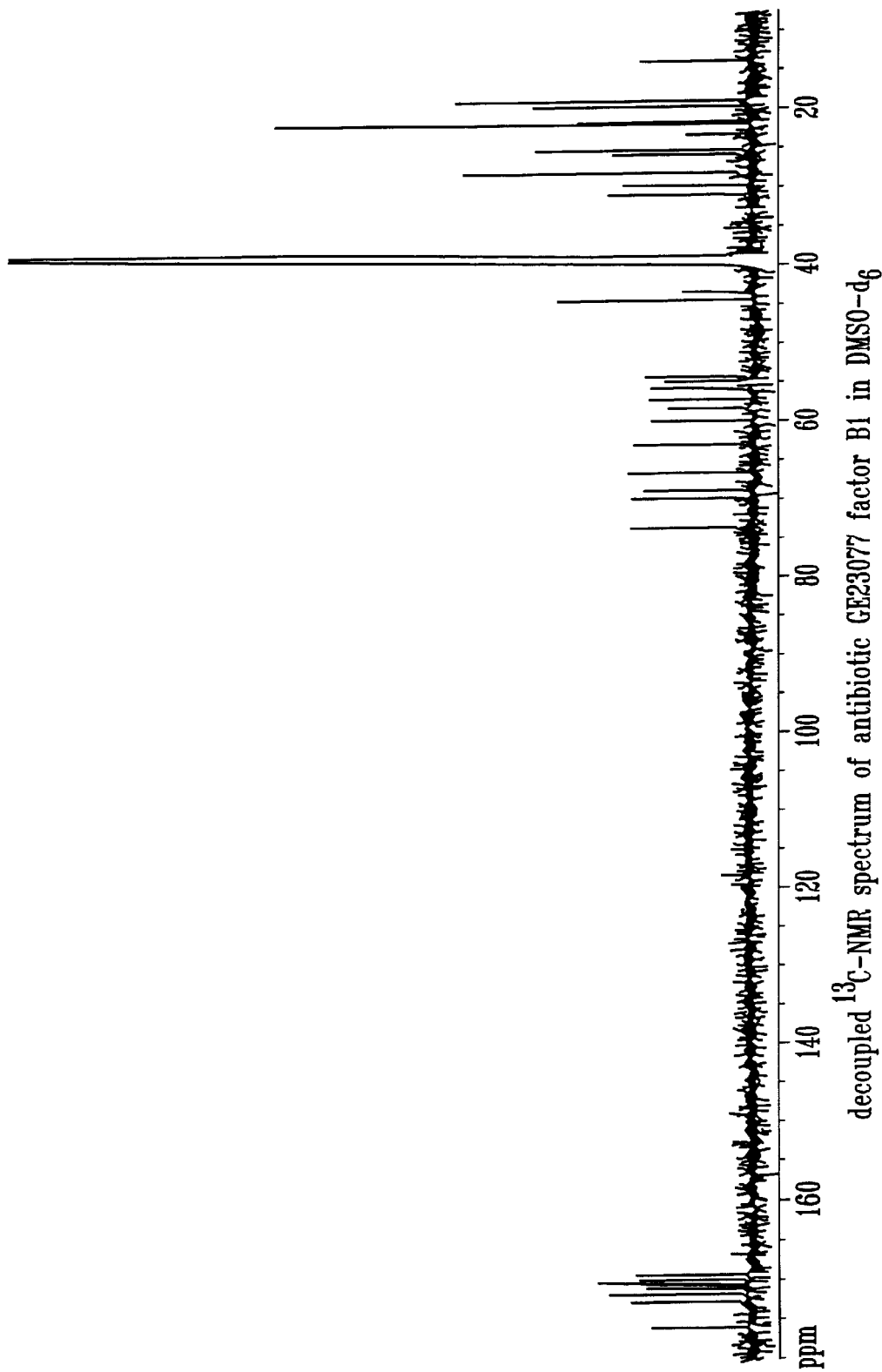
FIG. 7 decoupled $^{13}$C-NMR spectrum of antibiotic GE23077 factor B1 in DMSO-$d_6$

ANTIBIOTICS GE 23077, PHARMACEUTICALLY ACCEPTABLE SALTS AND COMPOSITIONS, AND USE THEREOF

The present invention concerns an antibiotic substance of microbial origin, arbitrarily denominated GE23077 complex and the individual factors that constitute it, namely GE23077 factor A1, GE23077 factor A2, GE23077 factor B1 and GE23077 factor B2, a mixture of said factors in any proportion, the pharmaceutically acceptable salts and compositions thereof, and their use as an antibacterial agent with a selective inhibitory activity against E. coli RNA polymerase.

Another object of the present invention is a process for preparing GE23077 complex, namely GE23077 factor A1, GE23077 factor A2, GE23077 factor B1 and GE23077 factor B2, a mixture of said factors in any proportion, hereinafter reported as GE23077 compounds.

STRAIN AND FERMENTATION

Actinomadura sp. DSMZ 13491 was isolated from a soil sample and deposited on May 22, 2000, with the DSMZ, (Deutsche Sammlung von Mikroorganismen und Zellkulturen GmbH, Mascheroder Weg 1b, D-38124 Braunschweig, Germany), under the provision of the Budapest Treaty. The strain was accorded accession number DSMZ 13491.

The production of compounds GE23077 factors A1, A2, B1 and B2, is achieved by cultivating an Actinomadura strain capable of producing them, i.e. Actinomadura sp. DSMZ 13491 or a variant or mutant thereof; isolating the resulting antibiotic from the mycelium and or the culture broth; purifying the isolated antibiotic; and separating the antibiotic four factors A1, A2, B1 and B2 by chromatographic means. Wishing to produce the GE23077 complex, the separating step is evidently unrequired. In any case, it is preferred to produce compounds GE23077 under aerobic conditions in an aqueous nutrient medium containing assimilable sources of carbon, nitrogen, and inorganic salts, purifying the resulting compounds by means of a chromatographic technique. Many of the nutrient media usually employed in the fermentation field can be used, however certain media are preferred.

Preferred carbon sources are glucose, xilose, cellobiose, cellulose, starch, corn meal, and the like. Preferred nitrogen sources are ammonia, nitrates, soybean meal, peptone, meat extract, yeast extract, tryptone, aminoacids, hydrolized casein and the like. Among the inorganic salts which can be incorporated in the culture media, there are the customary soluble salts capable of yielding sodium, potassium, iron, zinc, cobalt, magnesium, calcium, ammonium, chloride, carbonate, sulphate, phosphate, nitrate, and the like ions.

Preferably, the strain producing compounds GE23077 is pre-cultured in a fermentation tube or in a shake flask, then the culture is used to inoculate jar fermentors for the production of substantial quantities of substances. The medium used for the pre-culture can be the same as that employed for larger fermentations, but other media can also be employed. The strain producing compounds GE23077 can be grown at temperature between 20° C. and 40° C., preferably between 28° C. and 37° C.

During the fermentation, the GE23077 factors can be monitored by bioassay on susceptible microorganisms and/or by testing treated broth samples against or E. coli RNA polymerase and/or by HPLC analyses. Maximum production of GE23077 compounds generally occurs between the fourth and the seventh day of fermentation.

Compounds GE 23077 are produced by cultivating Actinomadura sp. DSMZ 13491 or a variant or mutant thereof producing compounds GE23077, and are found in the culture broths and/or in the mycelium.

MORPHOLOGICAL CHARACTERISTICS OF Actinomadura sp. DSMZ 13491

Actinomadura sp. DSMZ 13491 grows well on many standard solid media. Microscopic examination and cell dimensions were measured using the culture grown on one-tenth strength humic acid medium (H. Nonomura, 1984—Design of a new medium for isolation of soil actinomycetes. The Actinomycetes 18, 206–209).

After seven days incubation at 28° C., the strain revealed extensively branched vegetative hyphae (0.5 $\mu$m in diameter). No fragmentation was observed. The aerial mycelium contained slightly twisted chains of large spores (1.2–1.4 $\mu$m in diameter). No pseudosporangia were observed. Spore dimensions exceeded those of the mycelium, giving rise to a "segmented" appearance of the spore chain.

CULTURAL CHARACTERISTICS OF Actinomadura sp. DSMZ 13491

Actinomadura sp. DSMZ 13491 was grown for seven days in AF-MS liquid medium (see Example 1 for medium composition). The mycelium was harvested by centrifugation and washed twice in sterile one quarter strength Ringer's solution (OXOID). Subsequently, sufficient Ringer's solution was added to the mycelium to provide a suitable inoculum. Aliquots of the suspension were streaked in a cross-hatched manner onto various media recommended by Shirling and Gottlieb (E. B. Shirling and D. Gottlieb, 1966—Method for Characterization of Streptomyces species—Int. J. Syst. Bacteriol., 16, 313–340) and several media recommended by Waksman (Waksman S. A., 1961—The Actinomycetes—The Williams and Wilkins Co., Baltimore. Vol 2, pp 328–334).

The ability to use a variety of carbohydrates as a carbon and energy source was determined in ISP8 medium (Shirling and Gottlieb, ibid) containing the carbon source at a final concentration of 2% (w/v). All media were incubated at 28° C. for 21 days. Colour was assessed in natural daylight, using the Colour Atlas of Maerz and Paul (A. Maerz and M. R. Paul, 1950—A Dictionary of Colour, 2nd edition. McGraw-Hill Book Co. Inc., New York).

Colonial appearance, substrate and aerial mycelium colour and pigment production for strain GE23077 are recorded in Table I. Physiological characteristics of the strain are presented in Table II. The ability to utilise various carbohydrates for growth is shown in Table III.

TABLE I

Cultural characteristics of Actinomadura sp. DSMZ 13491

| MEDIUM | GROWTH[a] | VEGETATIVE MYCELIUM[b] | AERIAL MYCELIUM | DIFFUSIBLE PIGMENT |
|---|---|---|---|---|
| Bennet's | +++ | Pink patches, glutinous texture, translucent, amorphous with a diffuse edge | absent | None |
| Calcium malate | +++ | very pale pink, matt texture with a diffuse edge | white, abundant | None |
| Czapek Glucose | +++ | dull pink, glutinous texture, convoluted with an entire edge | absent | None |
| Czapek Sucrose | +++ | pink, glutinous texture with an entire edge | light pink, abundant | None |
| Egg albumin | +++ | very pale pink 6 opaque, glutinous texture, with edge entire; discolouration at growing edge | white | None |
| Glucose asparagine | ++ | light pink 6 white speckles, glutinous texture with edge entire | absent | None |
| Hickey and Tresner | +++ | pale yellow 6 opaque glutinous texture (matt at edges), convoluted with an entire edge | white, sparse | None |
| ISP2 | +++ | pale pink speckles, glutinous texture with edge entire | absent | None |
| ISP3 | +++ | pink (2-E-9), flat, smooth | Pale pink 6 white tufts | None |
| ISP4 | +++ | Deep pink (2-1-10), dimpled with edge entire | absent | None |
| ISP5 | ++ | very pale pink (2-C-1) speckles 6 opaque, glutinous texture with edges diffuse | white tufts, more concentrated at edges | None |
| ISP6 | +++ | pale yellow (deeper yellow patches) 6 opaque glutinous texture, convoluted with an entire edge | absent | None |
| ISP7 | +++ | pink 6 opaque, glutinous texture with edges diffuse | white tufts (mainly at growing edge) | None |
| Nutrient | +++ | Yellow 6 opaque glutinous texture, convoluted with an entire edge | white tufts (mainly at growing edge) | None |
| Oatmeal | ++ | very pale pink (4-C-1), flat, smooth, dimpled, amorphous | absent | None |
| Potato | +++ | pink (4-D-8), glutinous texture, convoluted with an entire edge | Absent | None |
| Sabouraud | ++ | opaque glutinous texture, with an entire edge | Absent | None |
| Skimmed milk | +++ | pink (4-F-8), glutinous texture, with an entire edge; clearing zones around growing edge | Absent | None |
| Potato glucose | +++ | pink (2-H-8), matt texture, convoluted | very light pink | None |

[a] ++: moderate growth; +++: good growth
[b] Codes in parenthesis indicate nearest available colour codes (Maerz & Paul, 1950)

TABLE II

CARBOHYDRATE UTILISATION

| CARBON SOURCE | GROWTH[a] |
|---|---|
| Arabinose | + |
| Cellobiose | ++ |
| Cellulose | ++ |
| Fructose | + |
| Galactose | + |
| Glucose | ++ |
| Inositol | + |
| Lactose | + |
| Maltose | + |
| Mannitol | + |
| Mannose | + |
| Raffinose | + |
| Rhamnose | + |
| Ribose | + |
| Salicin | + |
| Sucrose | + |
| Xylose | ++ |

[a] + weak growth; ++ moderate growth

TABLE III

PHYSIOLOGICAL TESTS

| TEST | REACTION |
| --- | --- |
| Calcium malate digestion | negative |
| Starch hydrolysis | positive |
| Tyrosine reaction (melanin) | positive |

CHEMOTAXONOMICAL CHARACTERISTICS OF Actinomadura sp. DSMZ 13491

Actinomadura sp. DSMZ 13491 was grown in Sauton's medium for four weeks and the mycelium harvested, washed three times with sterile distilled water and subsequently freeze-dried. The stereoisomeric form of the diaminopimelic acid (DAP) was determined according to the method of Staneck and Roberts, (J. L. Staneck and G. D. Roberts, Simplified approach to identification of aerobic actinomycetes by thin-layer chromatography, Appl. Microbiol. 28, 226–231, 1974).

The whole cell sugar pattern was determined according to Saddler et al. (Saddler G. S., P. Tavecchia, S. Lociuro, M. Zanol, L Colombo and E. Selva. Analysis of madurose and other actinomycete whole cell sugars by gas chromatography. J. Microbiol. Meth., 14, 185–191, 1991).

Isoprenoid quinones were extracted and purified using the small scale integrated procedure of Minnikin et al. (D. E. Minnikin, A. G. O'Donnell, M. Goodfellow., G. Alderson, M. ALhalye, A. Schaal and J. H. Parlett. An integrated procedure of isoprenoid quinones and polar lipids. J. Microbiol. Meth. 2, 233–241, 1984).

The menaquinones were separated by HPLC and identified by their retention behaviour according to their isoprenylic chain length and degree of saturation, as described by Kroppenstedt (R. M. Kroppenstedt, Separation of bacterial menaquinones by HPLC using reverse phase RP18 and a silver loaded ion exchanger as stationary phase. J. Liquid. Chromat. 5: 2359–2367, 1982).

Polar lipids were extracted, examined by two dimensional thin layer chromatography and identified using published procedures (D. E. Minnikin, A. G. O'Donnell, M. Goodfellow, G. Alderson, M. Athalye, H. Schaal and J. H. Parlett. An integrated procedure of isoprenoid quinones and polar lipids. J. Microbiol. Meth. 2, 233–241, 1984).

For the extraction of fatty acids, the wet biomass was extracted using minor modifications (L. D. Kuykendall, M. A. Roy, J. J. O'Neill and T. E. Devine, Fatty acid, antibiotic resistance, and deoxyribonucleic acid homology groups of Bradyrhizobium japonicium, Int. J. System. Bact. 38, 351–361, 1988) of the method of Miller (L. T. Miller, A single derivatization method for bacterial fatty acid methyl esters including hydroxy acids, J. Clin. Microbiol. 16, 584–586, 1982). Analysis were carried out as described by Kroppenstedt (R. M. Kroppenstedt, E. Stackebrandt and M. Goodfellow, Taxonomic revision of the actinomycete genera Actinomadura and Microtetraspora, System. Appl. Microbiol. 13, 148–160, 1990) and data examined using the Microbial Identification System (L. T. Miller, ibid).

The strain DSMZ 13491 contains meso-2,6-diaminopimelic acid. Madurose is present in the whole-cell hydrolysate. As shown in FIG. 1, the more abundant menaquinone is MK-9 ($H_6$) followed by smaller portions of MK-9($H_4$) and MK-9($H_8$). Among polar lipids, phosphatydilinositol, phosphatidylinositolmanosides, phosphatydilglycerol and diphosphatydilglycerol are identified in the chloroform methanol extracts. The following branched, saturated and unsaturated fatty acids plus tuberculostearic acid were detected.

Iso-15/17 Anteiso-15/17 Iso-16 10-Me16 10-Me17 10-Me18 2-OH –/– –/– + (+) + ++ –

(+): 1–5%; +: 5–15%; ++: 15–30%;

Iso-16: iso-hexadecanoic acid or 14-methylpentadecanoic acid;

10-Me-18: tuberculostearic acid;

2-OH-16: 2-hydroxy-palmitic acid.

IDENTITY OF STRAIN GE23077

The strain producing compounds GE23077 is assigned to the genus Actinomadura because of the following morphological and chemical characteristics:

- the formation of a branched not fragmented vegetative myceliurn and of short chains of arthrospores;
- the presence of meso-2,6-diamincpimelic acid in the cell wall and of madurose in the whole cell hydrolizate. This is characteristic of Chemotype IIIB according to Lechevalier and Lechevalier (H. A. Lechevalier and M. P. Lechevalier, A critical evaluation of the genera of aerobic actinomycetes, pp. 393–405; in: The Actinomycetales, H. Prausers ed., Jena, Gustav Fischer Verlag 1970);
- the composition of polar lipids according to the Phospholipid type 1 sensu Lechevalier et al. (H. A. Lechevalier, C. De Brieve and M. P. Lechevalier, Chemotaxonomy of aerobic actinomycetes: phospholipid composition, Biochem. Syst. Ecol. 5: 246–260, 1977) and of Menaquinones type 4B2 according to Kroppensdedt (R. M. Kroppenstedt, Separation of bacterial menaquinones by HPLC using reverse phase RP18 and a silver loaded ion exchanger as stationary phase, J. Liquid Chromat. 5: 2359–2367, 1982; R. M. Kroppenstedt, E. Stackebrandt and M. Goodfellow, Taxonomic revision of the actinomycete genera Actinomadura and Microtetraspora, System. Appl. Microbiol. 13, 148–160, 1990);
- the fatty acid profile of 3a Type according to Kroppenstedt and Goodfellow (R. M. Kroppenstedt and M. Goodfellow; The family Thermomonosporaceae, pp.1085–1114, in: The Prokariotes, Vol II, A. Balows, H. Truper, M. Dworkin, W. Harder and K. H. Schleifer eds; New York, Springer-Verlag, 1991).

As with other microorganisms, the characteristics of strain producing compounds GE23077 are subject to variation. For example, artificial variants and mutants of the strain can be obtained by treatment with various known mutagens, such as U.V. rays, and chemicals such as nitrous acid, N-methyl-N'-nitro-N-nitrosoguanidine, and many others. All natural and artificial variants and mutants of strain Actinomadura sp. DSMZ 13491 are deemed equivalent to it for the purpose of this invention and therefore within the scope of invention.

The antibiotic may be recovered from the fermented broth, both from the mycelium and the supernatant fraction.

EXTRACTION AND PURIFICATION OF GE23077 COMPOUNDS

The recovery of GE23077 complex from the fermentation broths of the producing microorganism is conducted according to known per se techniques such as extraction with solvents, precipitation by adding non-solvents or by changing the pH of the solution, partition chromatography, reverse-phase partition chromatography, ion-exchange chromatography, molecular exclusion chromatography and the like.

A procedure for recovering the antibiotic substance of the invention from the fermentation broth includes extraction of GE23077 complex or the salts thereof, with water-immiscible organic solvents, followed by precipitation from the concentrated extracts, possibly by adding a precipitating agent.

The term "water-immiscible solvent" as used in this application, is intended to have the meaning currently given to it in the art and refers to solvents that, at the conditions of use, are slightly miscible or practically immiscible with water in a reasonably wide concentration range, suitable for the intended use.

Examples of water-immiscible organic solvents that can be used in the extraction of the compounds of the invention from the fermentation broths are: alkanols of at least four carbon atoms which may be linear, branched or cyclic such as n-butanol, 1-pentanol, 2-pentanol, 3-pentanol, 1-hexanol, 2-hexanol, 3-hexanol, 3,3-dimethyl-1-butanol, 4-methyl-1-pentanol, 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopenthyl-1-propanol, cyclohexanol, cycloheptanol, cyclooctanol, 2,3-dimethylcyclohexanol, 4-ethylcyclohexanol, cyclooctylmethanol, 6-methyl-5-hepten-2-ol, 1-nonanol, 2-nonanol, 1-decanol, 2-decanol, and 3-decanol; ketones of at least five carbon atoms such as methylisopropylketone, methylisobutylketone, methyl-n-amylketone, methylisoamylketone and mixtures thereof.

As known in the art, product extraction may be mproved by adjusting the pH at an appropriate value, and/or by salting and/or by adding a proper organic salt forming an ion pair with the antibiotic which is soluble in the extraction solvent. As known in the art, phase separation may be improved by salting. When, following an extraction, an organic phase is recovered containing a substantial amount of water, it may be convenient to azeotropically distill water from it. Generally, this requires adding a solvent capable of forming minimum azeotropic mixtures with water, followed by the addition of a precipitating agent to precipitate the desired product, if necessary. Representative examples of organic solvents capable of forming minimum azeotropic mixtures with water are: n-butanol, benzene, toluene, butyl ether, carbon tetrachloride, chloroform, cyclohexane, 2,5-dimethyl furan, hexane, and m-xylene; the preferred solvent being n-butanol. Examples of precipitating agents are petroleum ether, lower alkyl ethers, such as ethyl ether, propyl ether, and butyl ether, and lower alkyl ketones such as acetone.

According to a preferred procedure for recovering of GE23077 complex, the filtered fermentation broths can be contacted with an adsorption matrix followed by elution with a polar water miscible solvent or a mixture thereof, concentration to water residue under reduced pressure, extraction with water-immiscible solvents, and precipitation with a precipitating agent of the type already mentioned above.

Examples of adsorption matrixes that can be conveniently used in the recovery of the compounds of the invention, are polystyrene or mixed polystyrene-divinylbenzene resins (e.g. M112 or S112, Dow Chemical Co.; Amberlite XAD2 or XAD4, Rohm & Haas; Diaion HP 20, Mitsubishi Chemicals), acrylic resins (e.g. XAD7 or XAD8, Rohm & Haas), polyamide resins such as polycaprolactames, nylons and cross-linked polyvinylpyrrolidones (e.g. Polyamide-CC 6, Polyamide-SC 6, Polyamide-CC 6.6, Polyamide-CC 6AC and Polyamide-SC 6AC, Macherey-Nagel & Co., west Germany; PA 400, M. Woelm AG, West Germany; and the polyvinylpirrolidone resin PVP-CL, Aldrich Chemie GmbH & Co., KG, West Germany), controlled pore cross-linked dextrans (e.g. Sephadex LH-20, Pharmacia Fine Chemicals, AB), and charcoal.

Preferably, polystyrene resins are employed, particularly preferred being the S112 (Dow Chemical Co.).

The preferred solvent for eluting GE23077 complex from the adsorption matrix depends on the specific stationary phase. In the case of polystyrene resins, polystyrene-divinylbenzene resins, acrylic resins or polyamide resin a preferred eluent is a water miscible solvent or its aqueous mixtures; in the case of charcoal a preferred eluent is a lower ketone such as acetone or a lower alcohol such as methanol. The aqueous mixtures can contain buffers at appropriate pH value.

The term "water-miscible solvent" as used in this application, is intended to have the meaning currently given in the art of this term and refers to solvents that, at the conditions of use, are miscible with water in a reasonably wide concentration range. Examples of water-miscible organic solvents that can be used in the elution of the compounds of the invention are: lower alkanols, e.g. ($C_1$–$C_3$) alkanols such as methanol, ethanol, and propanol; phenyl ($C_1$–$C_3$) alkanols such as benzyl alcohol; lower ketones, e.g. ($C_3$–$C_4$) ketones such as acetone and ethyl methyl ketone; cyclic ethers such as dioxane and tetrahydrofuran; glycols and their products of partial etherification such as ethylene glycol, propylene glycol, and ethylene glycol monomethyl ether, lower amides such as dimethylformamide and diethylformamide; acetic acid, dimethylsulfoxide and acetonitrile.

Purification of the crude GE23077 compounds, can be accomplished by any of the known per se techniques but is preferably conducted by means of chromatographic procedures.

Examples of these chromatographic procedures are those reported in relation to the recovery step and include also chromatography on stationary phases such as silica gel, alumina, activated magnesium silicate, and the like, with an organic eluting phase made of organic solvents including halogenated hydrocarbons, lower alkanols, ethers, higher ketones and mixtures thereof, or reverse phase chromatography on silanized silica gel having various functional derivatizations and eluting with an aqueous mixture of water-miscible solvents of the kind mentioned above.

Another way of purification is the chromatography on ion-exchange resin column. The elution can be conducted by a variation of pH or ionic-strength.

Conveniently, also the so called steric exclusion chromatography technique can be employed with good purification results. In particular, controlled pore cross-linked dextrans wherein most hydroxyl groups are alkylated, e.g. Sephadex LH-20 (Pharmacia Fine Chemicals, AB), are usefully employed in this technique.

For instance, medium pressure liquid chromatographic separation systems may be employed, using reverse phase chromatography on RP-8 or RP-18 functionalised silica gel and eluting with a sodium sulphate buffer.

As usual in this field, the production as well as the recovery and purification steps may be monitored by a variety of analytical procedures including HPLC and/or bioassay with a susceptible microorganisms and/or the inhibition assay of *E. coli* RNA polymerase.

The purification of individual factors A1, A2, B1 and B2 may be conveniently carried out by semipreparative HPLC of the GE23077 complex preparations.

A preferred preparative HPLC technique for the isolation of pure GE23077 factors A1, A2, B1 and B2 is performed on a semipreparative HPLC instrument (Shimadzu-LCBA) equipped with a 250×10 mm Supelcosil LC8 column, 5 μm, (Supelco Inc; Bellefonte, USA), eluted at 4 ml/min flow rate with a 25 min linear gradient from 50% to 80% of phase B, followed by 5 min elution with 80% of phase B. Phase A is methanol: 100 mM ammonium sulphate pH 7 buffer 5:95 (v/v), and Phase B is methanol:water 2:8 (v/v). UV detection is at 230 nm. The eluates of repeated chromatographic runs containing the separated GE23077 factors are pooled according to their content and are concentrated under reduced pressure to aqueous solutions, which are freeze-dried yielding purified GE23077 factors A1, A2, B1 and B2.

As usual in this field, the production as well as the recovery and the purification steps may be monitored by a variety of analytical procedures including bioassay with susceptible microorganisms and/or inhibition tests on bacterial RNA polymerase, and/or TLC and/or HPLC procedures. A preferred analytical HPLC technique is performed on a HP 1090 instrument equipped with a 250×4.6 mm column packed with C18 Ultrasphere ODS 5 $\mu$m stationary phase (Beckmann Co.), eluted at 1 ml/min flow rate with mixture of phase A and B. Phase A was methanol:100 mM ammonium sulphate buffer 5:95 (v/v) and phase B was methanol:water 20:80 (v/v). Elution was carried out with a linear gradient from 50% to 80% of phase B in 20 min; 80% of phase B for 5 min. Typical retention times of the four GE23077 factors are: 14.4 (A1), 16.5 (B1), 19.4 (A2), 21.3 (B2).

The GE23077 complex is constituted of two couples of isomers: factors A1, A2 and factors B1, B2. It was observed that the individual pure Factor A1 and Factor A2, when kept in water solution or in mixtures of water miscible solvents and water solutions, reach an equilibrium state between them. The same behaviour was observed for pure Factor B1 and Factor B2. The equilibration rate was accelerated at acidic and basic pHs. Recording the NMR spectra of the GE 23077 factors A2 and B2 in DMSO, it has further been found that they fully converted (it took 12 hours for A2 and few minutes for B2, both at room temperature) into factors A1 and B1, respectively. Accordingly, if recorded after complete conversion, the spectra relating to factors A2 and B2 correspond to the ones of the factors A1 and B1, respectively.

Since compounds GE23077 complex and its factors contain acid functions, they are capable of forming salts with suitable bases according to conventional procedures. The antibiotics, when obtained in the acid form, may be converted into a corresponding non-toxic pharmaceutically acceptable salt. Suitable salts include the alkali and alkaline earth metal salts, typically the sodium, potassium, calcium and magnesium salts, and the ammonium and substituted ammonium salts. Representative substituted ammonium salts include primary, secondary or tertiary (CI–C4) alkylammonium and hydroxy (CI–C4) alkylammonium salts and, according to an embodiment of the present invention, the benzathine, procaine, hydrabamine and similar water insoluble, non-toxic, pharmaceutically acceptable salts. Also preferred, within said class of salts, are the salts of the compounds of the present invention commonly represented as the basic addition salts, i.e. the salts with basic aminoacids such as arginine or lysine, or aminosugars such as glucosamine and the like.

The alkali and alkaline earth metal salts are prepared according to the usual procedures commonly employed for preparing metal salts. As an example, antibiotic GE23077 is dissolved into the minimum amount of a suitable solvent, typically a lower alkanol, the stoichiometric amount of a suitable selected base is gradually added to the obtained solution and the obtained salt is precipitated by the addition of a non-solvent. The resulting alkali or alkaline earth metal salt is then recovered by filtration or evaporation of the solvents.

Alternatively, these salts can be prepared in a substantially anhydrous form by lyophilization; in this case, aqueous solutions containing the desired salts, resulting from the salification of antibiotic GE23077 with a suitably selected alkali or alkaline earth metal carbonate or hydroxide in such a quantity as to obtain a pH comprised between 7.0 and 8.5 are filtered from any insolubles and lyophilized.

The organic ammonium salts can be prepared substantially following the above procedure by adding the properly selected amine to a solution of antibiotic GE23077 in a suitable solvent and then evaporating off the solvent and the excess of the amine reagent or by lyophilizing the concentrate solution.

The pharmaceutically acceptable salts so formed are also part of this invention. "Pharmaceutically acceptable" salts are salts which are useful in the therapy of warm-blooded animals.

The transformation of the compounds of the invention into the corresponding salts thereof, and viceversa, i.e. the transformation of a salt of a compound of the invention into the non-salt form are within the ordinary technical skill and are encompassed by the present invention.

PHISICO-CHEMICAL CHARACTERISTICS OF THE GE23077 COMPLEX

A) Ultraviolet absorption spectrum, in a water:methanol 1:1 (v/v) solution, shows end-absorption (maximum at 204 nm), with no significative shift of wavelength absorbance at neutral and acidic pH. Upon addition of KOH, the maximum shifted at 218 nm. The spectrum was recorded on a Perkin-Elmer spectrophotometer mod. Lambda 16.

B) Positive ion FAB mass spectrometry analysis shows peaks corresponding to $[M-H]^+$ of the components of the complex and having 804 and 806 m/z. The FAB mass spectrometry analysis was carried out on a Finnigan TSQ700 triple quadrupole mass spectrometer using a xenon atom gun, operating at 8 kV, 0.23 mA current and glycerol as ionization matrix.

C) Amino acid analysis of the acid hydrolysate which shows the presence of valine, serine, threonine, isoserine, glycine and 2,3 diaminopropanoic acid, and other unidentified fragments.

The GE23077 complex was treated for 24 hours at 105° C. with 500 $\mu$l of 6N HCl in the presence of phenol, using a Pico-Tag apparatus (Millipore-Waters Co.). The residue was diluted with water and freeze-dried. The mixture was then treated sequentially a) at 100° C. for 30 min with 200$\mu$l of 2.4N HCl in n-butanol, dried and then treated at 100° C. for 10 min with 100 ml of trifluoroacetic anhydride. The sample was then dried under nitrogen and dissolved in 100 ml of hexane, before submitting it to GC-MS analysis. The analysis was done using a Finnigan TSQ 700 triple stage GC/MS instrument with a SPB1 column, 30 mm×0.2 mm (Supelco Inc; Bellefonte, USA) having a 0.25 $\mu$m film thickness. The oven temperature was 60° C. for 1 minute followed by a gradient from 60° C. to 260° C, at 12° C./min; the carrier gas was helium at 8 Psi and split vent was at 80 ml/min; the injector temperature was 260° C. The Electron Impact (EI) conditions were: EI positive ionization; source temperature: 150° C.; electron energy: 70 eV and filament current: 400 ma. Chromatographic peaks were identified on the basis of their retention times and MS fragmentations.

D) Infrared absorption spectrum (shown in FIG. 2) which exhibits the following absorption maxima v $(cm^{-1})$: 3292; 3072; 2955; 2924 (nujol); 2853 (nujol); 1732; 1686; 1655; 1628; 1545; 1462; 1377; 1317; 1263; 1219; 1113; 1049; 978; 721. The spectrum was recorded in nujol mull with an IFS-48 Fourier Transform spectrophotometer.

E) Retention times of the four GE23077 factors: 14.16 min (A1), 16.56 min (B1), 20.90 min (A2), 22.71 min (B2), which were found by HPLC analysis under the following chromatographic conditions (method A):

Instrument: HP mod. 1090 (DAD detector);

Column: Beckmann ODS C18 (5 μm 250×4.6 mm);

Elution: Isocratic 15% Phase B;

Phase A: Ammonium formiate (2.5 g/l): Methanol (99:1 v/v);

Phase B: Ammonium formiate (2.5 g/l): Methanol (30:70 v/v);

Flow rate: 1.5 ml/min;

Detector: UV 230 nm.

F) THe $^1$H-NMR spectrum (shown in FIG. 3), was recorded at 600 mHz in DMSO-d$_6$.

9.00; 8.93; 6.34; 4.65; 4.47; 4.04; 3.99; 3.90; 3.88; 3.74; 3.53, 2.53; 1.95; 1.87; 1.71; 1.67; 0.96; 0.87; 0.85.

G) R$_f$ value of 0.7 when analyzed by TLC using silica gel plates Merck 5714 (E. Merck; Darmstadt F. R. Germany) and developing in ethanol:n-butanol:water 2:2:1 (v/v). Detection was by scrubbing portions of the the silica layer, by extracting with methanol and by testing with the RNA polymerase assay the extracts.

PHYSICO-CHEMICAL CHARACTERISTICS OF GE23077 FACTOR A1

A) positive ion FAB mass spectrometry analysis showed a peak corresponding to [M–H]$^+$ and had 804 m/z. The FAB mass spectrometry analysis was carried out on a Finnigan TSQ700 triple quadrupole mass spectrometer using a xenon atom gun, operating at 8 kV, 0.23 mA current and glycerol as ionization matrix.

B) $^1$H-NMR spectrum (shown in FIG. 4) was recorded at 600 MHz in DMSO-d$_6$ (hexadeuterodimethylsulfoxide) and exibits the following signals (in ppm) referenced to the residual peak of DMSO set at 2.5 ppm as internal standard: the values marked with an asterisk are overlapping of two $^1$H signals.

8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/3.49; 3.53,3.42/3.25; 2.50; 1.74; 1.70; 0.96; 0.94; 0.85.

C) $^{13}$C-NMR spectrum (shown in FIG. 5) was recorded at 150 MHz in DMSO-d$_6$ (hexadeuterodimethylsulfoxide) and exibits the following signals (in ppm) referenced to the residual peak of DMSO set at 39.5 ppm as internal standard: the values marked with an asterisk are overlapping of two $^{13}$C signals.

175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.9; 19.3; 19.2; 13.7; 12.3.

D) Factor A1 analysed by the method A shows a retention time of 14.16 min.

PHYSICO-CHEMICAL CHARACTERISTICS OF GE23077 FACTOR A2

A) positive ion FAB mass spectrometry analysis showed a peak corresponding to [M–H]$^+$ and had 804 m/z. The FAB mass spectrometry analysis was carried out on a Finnigan TSQ700 triple quadrupole mass spectrometer using a xenon atom gun, operating at 8 kV, 0.23 mA current and glycerol as ionization matrix.

B) HPLC analysis:

Factor A2 analyzed by the method A shows a retention time of 20.90 min.

C) $^1$H-NMR spectrum (recorded after complete conversion of factor A2 into factor A1, identical to the one shown in FIG. 4) was recorded at 600 MHz in DMSO-d$_6$ (hexadeuterodimethylsulfoxide) and exibits the following signals (in ppm) referenced to the residual peak of DMSO set at 2.5 ppm as internal standard: the values marked with an asterisk are overlapping of two $^1$H signals.

8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/3.49; 3.53,3.42/3.25; 2.50; 1.74; 1.70; 0.96; 0.94; 0.85.

D) $^{13}$C-NMR spectrum (recorded after complete conversion of factor A2 into factor A1, identical to the one shown in FIG. 5) was recorded at 150 MHz in DMSO-d$_6$ (hexadeuterodimethylsulfoxide) and exibits the following signals (in ppm) referenced to the residual peak of DMSO set at 39.5 ppm as internal standard: the values marked with an asterisk are overlapping of two $^{13}$C signals.

175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.9; 19.3; 19.2; 13.7; 12.3.

PHYSICO-CHEMICAL CHARACTERISTICS OF GE23077 FACTOR B1

A) positive ion FAB mass spectrometry analysis showed a peak corresponding to [M–H]$^+$ and had 806 m/z. The FAB mass spectrometry analysis was carried out on a Finnigan TSQ700 triple quadrupole mass spectrometer using a xenon atom gun, operating at 8 kV, 0.23 mA current and glycerol as ionization matrix.

B) The $^1$H-NMR spectrum (shown in FIG. 6) was recorded at 600 MHz in DMSO-d$_6$ (hexadeuterodimethylsulfoxide) and exibits the following signals (in ppm) referenced to the residual peak of DMSO set at 2.5 ppm as internal standard: the values marked with an asterisk are overlapping of two $^1$H signals.

9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84.

C) The $^{13}$C-NMR spectrum (shown in FIG. 7) was recorded at 150 MHz in DMSO-d$_6$ (hexadeuterodimethylsulfoxide) and exibits the following signals (in ppm) referenced to the residual peak of DMSO set at 39.5 ppm as internal standard: the values marked with an asterisk are overlapping of two $^{13}$C signals.

175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2.

D) HPLC analysis:

Factor B1 analysed by method A shows a retention time of 16.56 min.

PHYSICO-CHEMICAL CHARACTERISTICS OF GE23077 FACTOR B2

A) positive ion FAB mass spectrometry analysis showed a peak corresponding to [M–H]$^+$ and had 806 m/z. The FAB mass spectrometry analysis was carried out on a Finnigan TSQ700 triple quadrupole mass spectrometer using a xenon atom gun, operating at 8 kV, 0.23 mA current and glycerol as ionization matrix.

B) Factor B2 analysed by method A shows a retention time of 22.71 min.

C) The $^1$H-NMR spectrum (recorded after complete conversion of factor B2 into factor B1, identical to the one shown in FIG. 6) was recorded at 600 MHz in DMSO-d$_6$ (hexadeuterodimethylsulfoxide) and exibits the following signals (in ppm) referenced to the residual peak of DMSO set at 2.5 ppm as internal standard: the values marked with an asterisk are overlapping of two $^1$H signals.

9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84.

D) The $^{13}$C-NMR spectrum (recorded after complete conversion of factor B2 into factor B1, identical to the one shown in FIG. 7) was recorded at 150 MHz in DMSO-d$_6$ (hexadeuterodimethylsulfoxide) and exibits the following signals (in ppm) referenced to the residual peak of DMSO set at 39.5 ppm as internal standard: the values marked with an asterisk are overlapping of two $^{13}$C signals.

175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2.

On the basis of she physico-chemical data reported above, the following structure formula can be tentatively assigned to antibiotic GE23077 complex, which is a preferred embodiment of the invention together with the pharmaceutically acceptable salts thereof:

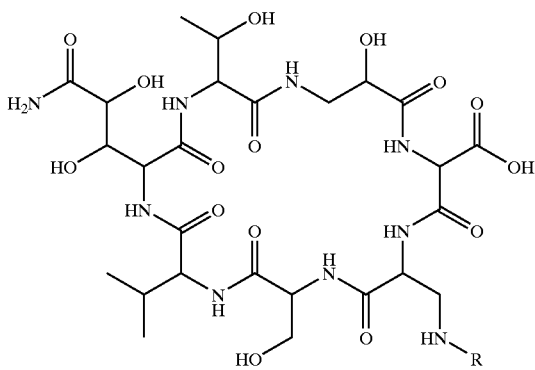

wherein
R is

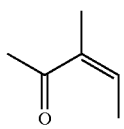

for factors A1 and A2
and R is

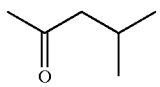

for factors B1 and B2 and the pharmaceutically acceptable salts thereof.

BIOLOGICAL ACTIVITY

Inhibition of RNA Polymerase

The inhibition of RNA polymerase was determined in a cell free transcription assay performed in standard U-bottom 96-well plates. The [H$^3$]-UTP incorporation in RNA was measured in the material precipitated upon addition of trichloroacetic acid (TCA). The reaction mixture contained 50 mM Tris-HCl (pH8), 50 mM KCl, 10 mM MgCl$_2$, 0.1 mM EDTA, 5 mM dithiothreitol (DTT), 10 μg/ml BSA, 20: g/ml calf thymus DNA, 1 mM ATP, 1 mM CTP, 1 mM GTP, 0.5 mCi $^3$H-UTP and 0.5 U of *E. coli* RNA polymerase enzyme (Epicentre Technology; Madison Wis.). 5 μl of the tested solution were added to 45 μl of reaction mixture, incubated at 37° C. for 15 minutes and then quenched with 150 μl of ice-cold 10% (w/v) TCA. After 30 min in ice, the well content was collected on glass-fiber filters (Filtermat A, Wallac) using a 96 wells cell harvester (Wallac) and radioactivity was determined in a β-Plate scintillation counter (Wallac). Count per min (CPM) values are transformed in % of RNA polymerase inhibition by using the following formula:

% of RNA polymerase=100−[(CPM compound−CPM blank)/ (CPM control−CPM blank)]*100 where: CPM compound is CPM in well with compound; CPM blank is CPM average in wells without enzyme template and CPM control is CPM average in wells without compound.

The GE23077 complex showed IC$_{50}$ of *E. coil* RNA polymerase at 0.02 μg/ml. A rifampicin resistant RNA polymerase (Promega; Madison Wis.) was inhibited with IC$_{50}$=0.04 μg/ml. Wheat germ RNA polymerase (Epicentre Technology; Madison Wis.) was inhibited at higher concentration (IC$_{50}$=100 pg/ml).

The individual GE23077 factors inhibited the *E. coli* RNA polymerase, showing IC$_{50}$=0.15 μg/ml (Factor A1); 0.035 μg/ml (Factor A2); 0.1 μg/ml (Factor B1) and 0.02 μg/ml (Factor B2).

ANTIMICROBIAL ACTIVITY

Antimicrobial activity of complex GE23077 was determined using microdilution method with standard U-bottom 96-well plates according to The National Committee for Clinical Laboratory Standards; Methods for Dilution Antimicrobial Susceptibility Tests for Bacteria that Grow Aerobically- Third Edition; Approved Standard. NCCLS document M7-A3 Vol.13 No. 25.

The media used were cation-adjusted Mueller Hinton Broth (CAMHB) for *Escherichia coli, Staphylococcus aureus, Moraxella catarrhalis, Bacillus subtilis, Mycobacterium smegmatis*; Todd Hewitt Broth (THB) for *Streptococcus pyogenes*; Brain Heart Infusion Broth+1% (v/v) supplement C (CBHI) for *Haemophilus influenzae*; GC base Broth+1% (v/v) Isovitalex for *Neisseria gonorrhoeae*; Tripticase Soy Broth+10% fetal calf serum (TB) for *Corynebacterrium jeikelum*; Terrific Broth (TB) buffered with 50 mM Sodium Phosphate (pH 7) for *E. coli* sp. and *E. coli* ATCC 25922. Unless otherwise indicated inocula were 10$^4$ CFU/ml. All strains were incubated at 35° C. in air, except *H. influenzae* and *N. gonorrhoeae* which were incubated in 5% CO$_2$. Incubation time was 18–24 hours except for *Moraxella catarrhalis, Neisseria gonorrhoeae, Haemophilus infiluenzae* and *Mycobacterium smegmatis* that were grown for 48 hours. Visual readings were performed after incubation and the MIC was defined as the lower concentration that completely inhibited growth of tested microorganisms.

GE23077 complex is not active against most of the bacteria tested although it inhibits the growth of three strains of *M. catarrhalis*, with MIC in the 4–8 μg/ml range. These strains are clinical isolates and are reported to have different levels of susceptibility to β-lactams, as reported below.

| Strain | Note |
|---|---|
| 3292 *Moraxella catarrhalis* -U503- | β-lactamase negative ampicillin susceptible |

-continued

| Strain | Note |
| --- | --- |
| 3293 Moraxella catarrhalis -U501- | BRO1 β-lactamase producer, ampicillin-resistant |
| 3294 Moraxella catarrhalis -W501- | BRO2 β-lactamase low level producer, ampicillin resistant |

GE23077 complex shows also marginal activity (MIC 256 µg/ml) against *N. gonorrhoeae* ISM68/126, clinical isolate.

The individual factors A1, A2, B1 and B2 also inhibit *M. catarrhalis*. This was demonstrated by collecting the eluates of an HPLC fractionation of the GE23077 complex, by concentrating them under vacuum and by testing their activity against *M. catarrhalis*. The fractions containing the separated factors A1, A2,B1 and B2 inhibited the test microorganism.

Compounds GE23077 are thus inhibitors of *M. catarrhalis*.

*M. catarrhalis* is a recognized important pathogen of humans. It is a common cause of respiratory tract infections, particularly otitis media in children and lower respiratory tract infections in the eldery. The widespread production of β-lactamase enzyme renders *M. catarrhalis* resistant to the penicillins (K. McGregor, B. J. Chang, B. J. Mee and T. V. Riley. Moraxella catarrhalis: clinical significance, antimicrobial susceptibility and BRO beta-lactamases. Eur. J. Microbiol. Infect. Dis. 17, 219–34, 1998). *M. catarrhalis* has been recently accepted as the third commonest pathogen of the respiratory tract after *Streptococcus pneumoniae* and *Haemophilus influenzae* (M. C. Enright and H. McKenzy, Moraxella (Branhamella) catarrhalis—Clinical and molecular aspect of a rediscovered pathogen, J. Med. Microbiol. 46, 360–71, 1997).

The compounds of the invention can be administered, as a pharmaceutically acceptable composition, as such or in admixture with a pharmaceutically acceptable carrier and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

The compounds of the invention can be accordingly used as a medicament; the single factors A1, A2, B1 and B2 can be utilized alone or as a mixture of two or more of them, in any proportion. Said mixture may be obtained by mixing predetermined amounts of two or more factors. Alternatively, mixtures of the four factors can be directly obtained from the isolation of the fermentation product of Actinomadura sp. DSMZ 13491 according to the above described process. An example of said mixture is the C-E23077 complex which is constituted by the factors A1, A2, B1 and B2.

Preferably, the compounds of the invention, are formulated into formulations suitable for parenteral administration, according to procedures known per se in the art and reported in reference books such as the one mentioned above.

For instance, a compound of the invention is formulated with a solubilising agent, such as polypropylene gliycol or dimethylacetamide, and a surface-active agent, such as polyoxyethylene sorbitan mono-oleate or polyethoxylated castor oil in sterile water for injection.

An example of a typical formulation for parenteral administration contains 10 mg of antibiotic G72307, factors per ml of final preparation, 10–20% of a surface-active agent, which may be a polyoxyethylene sorbitan fatty acid ester, a polyoxyethylene castor oil derivative or a polyoxyethylene hydrogenated castor oil derivative and 0–20%, preferably 10–20%, of a solubilizing agent such as propylene glycol, dimethylacetamide, dimethylformamide, ter-butyl-N-hydroxycarmabate, 1,2-, 1,3-, or 1,4-butandiol, ethyl oleate, tetrahydrofurfuryl-polyethylene-glycol 200, dimethyl isosorbide, benzyl alcohol and the like. A preferred solubilizing agent is propylene glycol.

Polyoxyethylene sorbitan fatty acid esters are commercially available and some of them are traded under the trade name "Tween". They are also known with the non-proprietary name of "polysorbates". Examples of them are polysorbate 20, 21, 40, 60, 61, 65, 80, 81 and 85. Preferred for use in the formulaticns of the invention is polysorbate 80 [sorbitan mono-9-octadecanoate, poly-(oxy-1,2-ethanediyl) derivatives].

Polyoxyethylene castor oils and polyoxyethylene hydrogenated castor oils are also commercially available. Some of them are traded with the trade name "Cremophor". Examples of such compounds are those known as Cremophor EL (polyethoxylated castor oil), Cremophor RH 40 (polyethoxylated hydrogenated castor oil), Cremophor RH 60 (PEG 60 hydrogenated castor oil) or Emophor EL-719 (polyoxyethylated vegetable oil).

Preferably, a formulation for injection should have a pH in the range of 7±0.5. If necessary, it might be advisable to adjust the pH of the preparation with a suitable buffering agent. Conveniently, TRIS (i.e. trihydroxymethylaminomethane) or phosphate can be used as buffering agents. A preferred formulation fox parenteral administration includes the following excipients: propylene glycol from 5 to 20%, preferably 10–20%. Generally, these formulations can be preparec by dissolving the active ingredient into the organic solvent, then adding the surface active ingredient, and finally diluting to the desired volume with sterile water for injection.

Alternatively, the active ingredient may be prepared as a lyophilized powder for reconstitution before use.

If the lyophilized material is prepared starting from a mixture containing the active ingredient and the surfactant, such as polyethylene glycol 60 hydrogenated castor oil, it can conveniently be reconstituted with the aqueous medium alone, without addition of an organic solvent.

Optionally, a common lyophilization aid can be added, if necessary, to obtain a lyophilized material in powder form. Preferably, all these formulations are used for i.v. administration in the treatment of any infection involving a microorganism susceptible to the antibiotic of the invention.

Alternatively, the active ingredient may be prepared as a lyophilized powder for reconstitution before use. If the lyophilized material is prepared starting from a mixture containing the active ingredient and the surfactant, such as polyethylene glycol 60 hydrogenated castor oil, it can conveniently be reconstituted with the aqueous medium alone, without addition of an organic solvent. Optionally, a common lyophilization aid can be added, if necessary, to obtain a lyophilized material in powder form.

Preferably, all these formulations are used for i.v. administration in the treatment of any infection involving a microorganism susceptible to the antibiotic of the invention. The antibiotic may also be used in a suitable pharmaceutical form such as a capsule, a tablet or an aqueous suspension.

The dosage of the active ingredient depends on many factors which include type, age and conditions of the patient, specific active ingredient and formulation selected for the administration, administration schedule, etc. In general, effective antimicrobial dosages are employed per single unit dosage form. Repeated applications/administrations, e.g. from 2 to 6 times a day, are in general preferred. An effective dosage may be in general in the range 0.5–50 mg/kg body weight/day. A preferred topic preparation is an ointment containing from 1% to 10% of a compound of the present invention.

Anyway, the prescribing physician will be able to determine the optimal dosage for a given patient in a given situation.

BRIEF DESCRIPTION OF THE DRAWINGS

FIG. 6 represents the $^1$H-NMR of antibiotic GE23077 factor B5, measured at 500 MHz in DMSO-$d_6$;

FIG. 7 represents the $^{13}$C-NMR of antibiotic GE23077 factor B1 at 125 MHz in DMSO-$d_6$;

Figure 1:
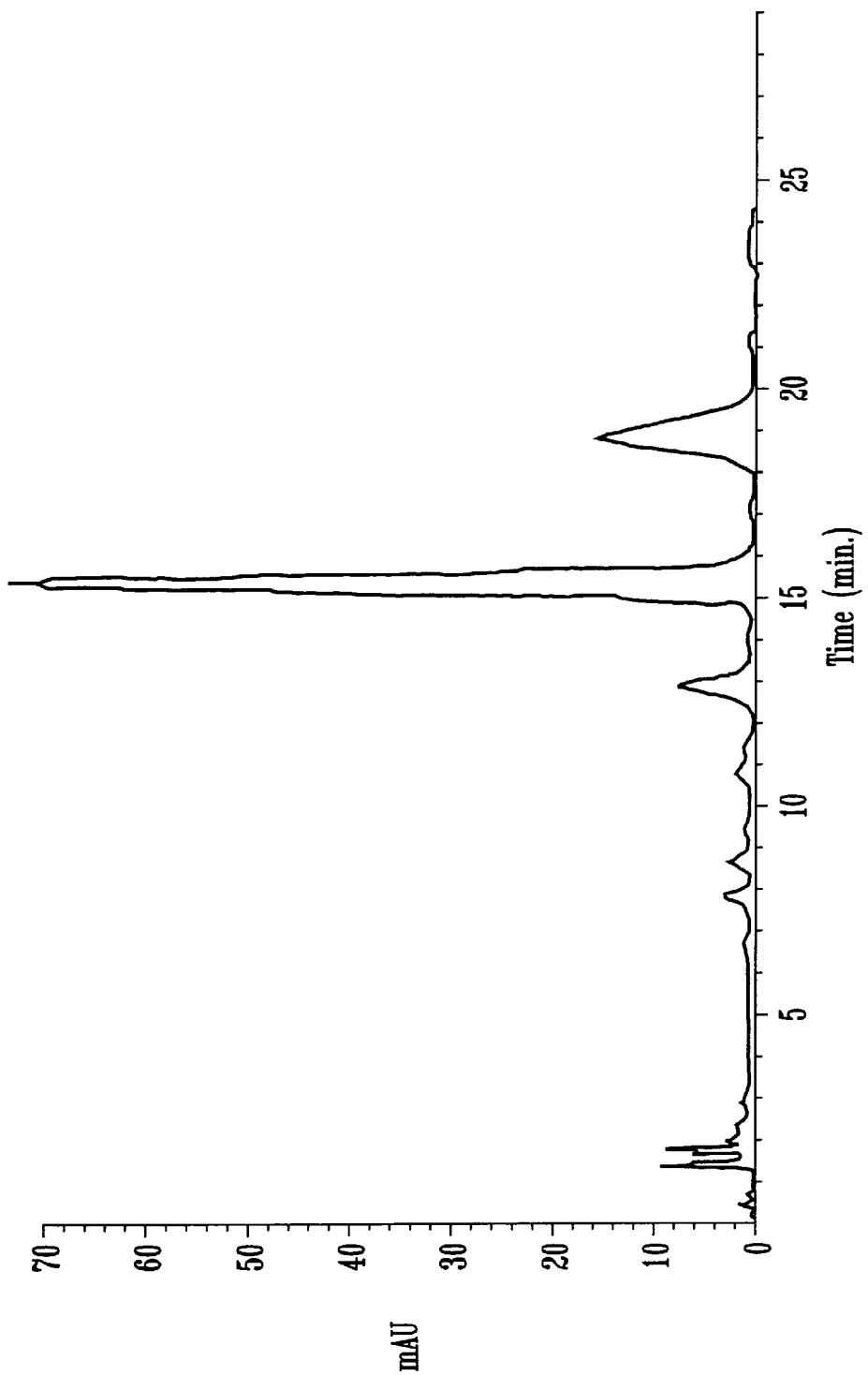
FIG. 1 represents the chromatographic profile of menaquinones from strain DSMZ 13491.
Figure 2:
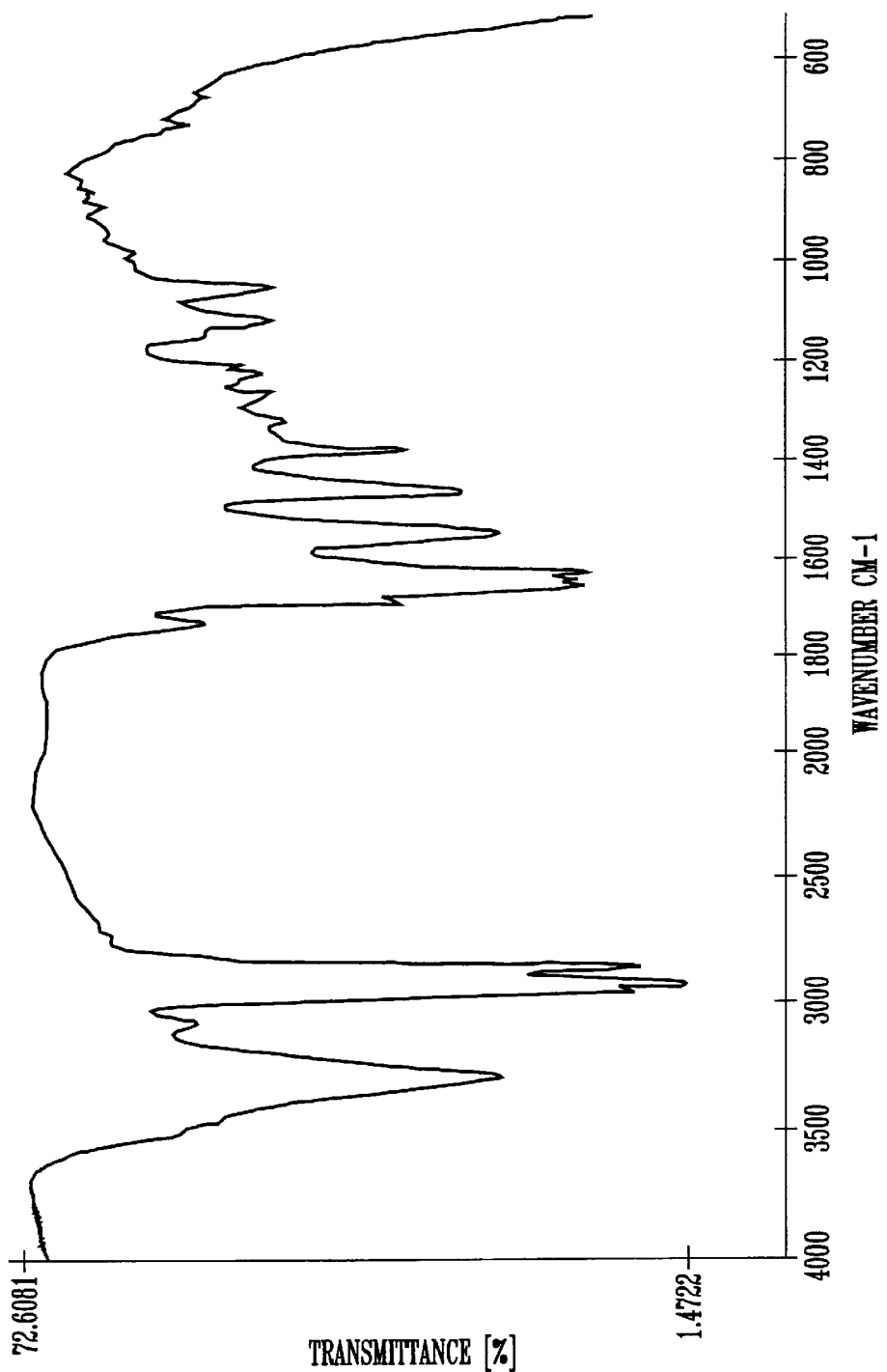
FIG. 2 represents the I.R. absorption spectrum of antibiotic GE23077 complex in nujol mull.
Figure 3:
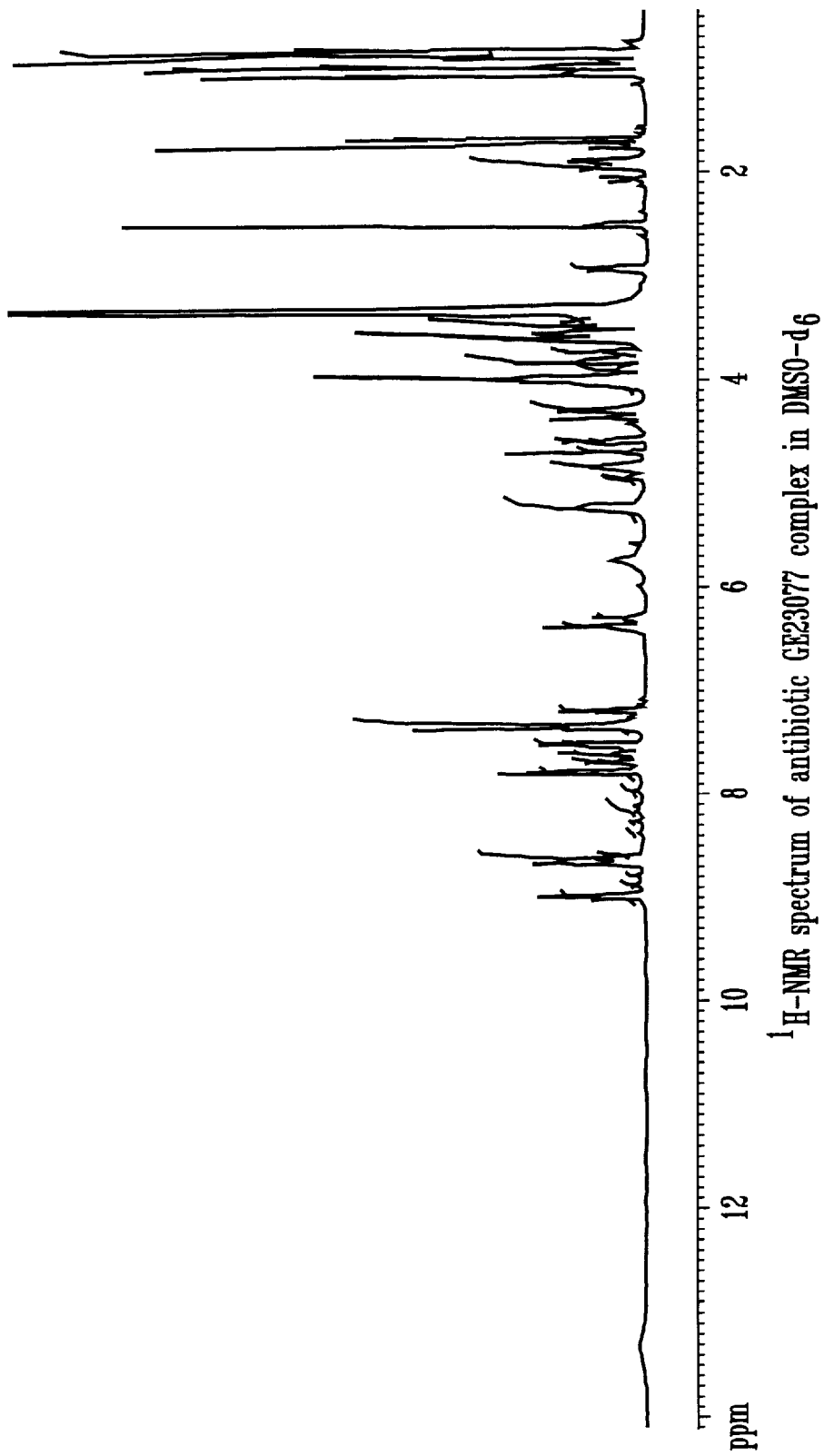
FIG. 3 represents the $^1$H-NMR of antibiotic GE23077 complex, measured at 500 MHz in DMSO-$d_6$.
Figure 4:
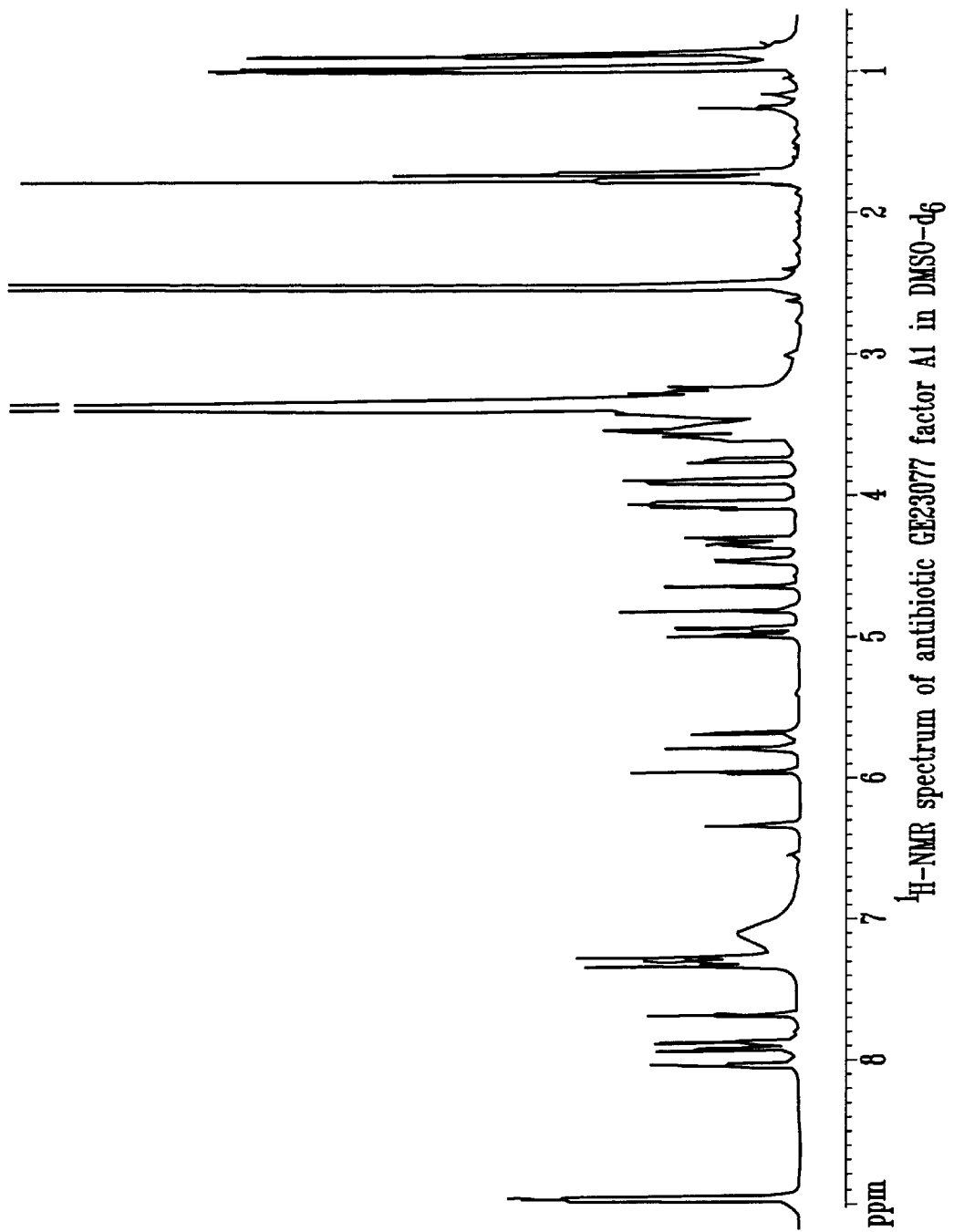
FIG. 4 represents the $^1$H-NMR of antibiotic GE23077 factor A1, measured at 500 MHz in DMSO-$d_6$.
Figure 5:
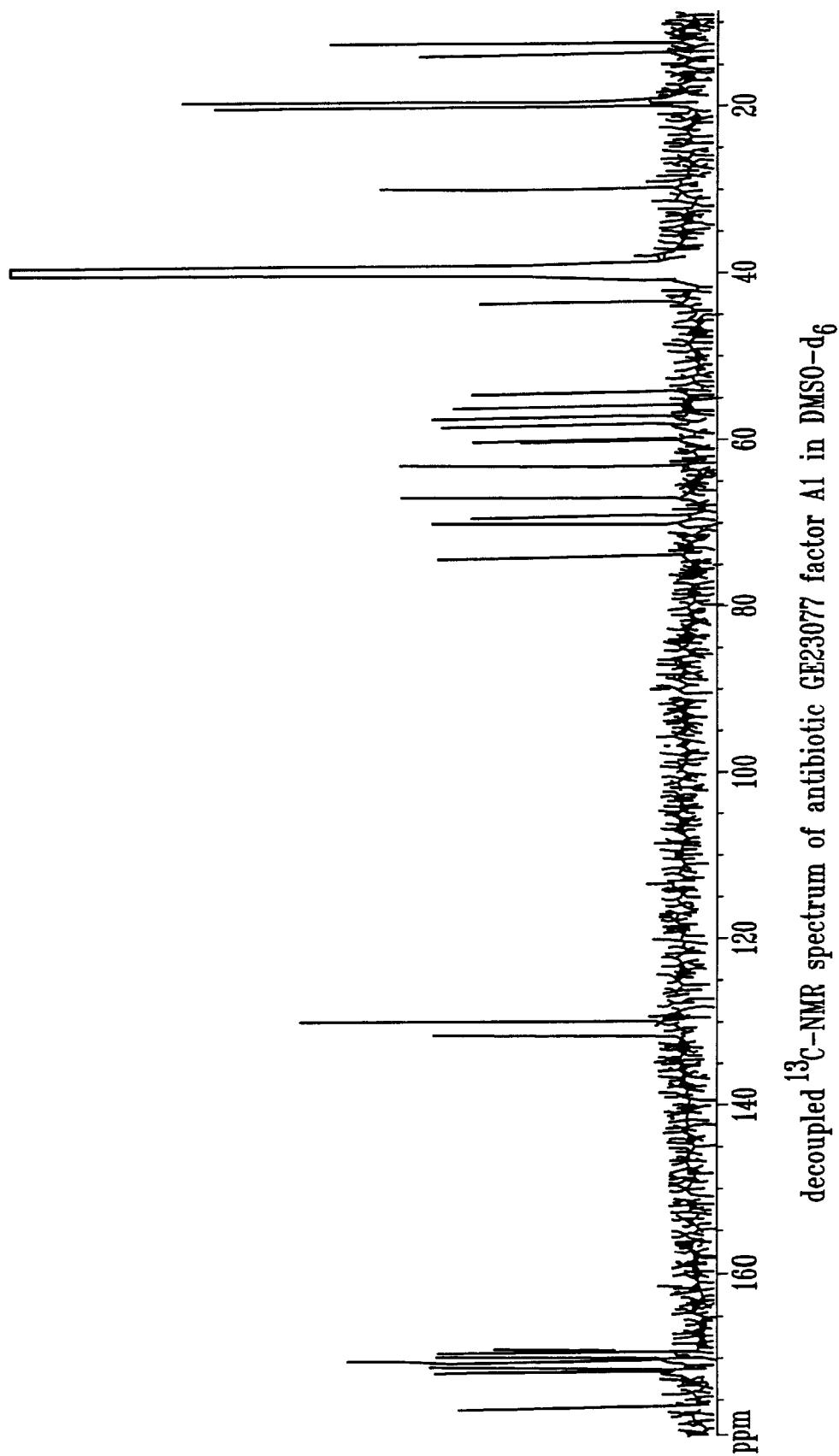
FIG. 5 represents the $^{13}$C-NMR of antibiotic GE23077 factor A1 at 125 MHz in DMSO-$d_6$.

The following examples further illustrate the invention without limiting it.

EXAMPLE 1

Fermentation Method for Production of GE23077 Complex

Actinomadura sp. DSMZ 13491 was maintained on Oatmeal agar slant culture. These slants served as the source of inoculum for 100 ml of medium A contained in 500 ml Erlenmeyer flasks. Medium A was composed of glucose (20 g), yeast extract (2 g), soybean flour (8 g), NaCl (1 g), calcium carbonate (4 g) and distilled water to 1000 ml. The pH of the medium was adjusted to 7.3 before sterilization by autoclaving at 121° C. for 30 minutes. After inoculation, the flasks were incubated on a rotary shaker (200 rpm, 2-inch throw) at 28° C. for 72 hours. After the incubation period, 2% (v/v) transfers were made from the grown culture flasks to a 7 l jar fermenter containing 4 l of medium A. The culture was incubated at 28° C. for 48 hours with 900 rpm stirring and 0.5 v/v/min aeration and then transferred into a fermenter containing 200 l of medium A. The fermentation was continued for 96 hours at 29° C. with 200 rpm stirring and 0.5 v/v/min aeration. The production of the antibiotic was monitored by analytical HPLC and with the assay of RNA polymerase inhibition.

EXAMPLE 2

Method for Recovery and Purification of Complex GE23077

The broth of a 200 l fermentation was harvested after 96 hours and the mycelium was removed by filtration with Hyflo filter matrix. The filtrate wa: stirred batch-wise for 3 hours with 6 l of S112 polystyrene resin (The Dow Chemical Co.). The resin was then recovered, washed with water and eluted with 15.5 l of a mixture of acetone:water:n-butanol 8:1:1 (v/v). The eluted fractions containing GE23077 complex were concentrated under reduced pressure and the aqueous residue applied at the top of a 47×7 cm column containing 1.6 l of S112 polystiyenic resin (The Dow Chemical Co.), which was previously equilibrated with 0.1M $(NH_4)_2SO_4$. The column was eluted at 25 ml/min flow rate, with a 240 min linear gradient from 0% to 100% of phase B in phase A. Phase A was 100 mM ammonium sulphate buffer (pH 7) and phase B was water. The pooled fractions containing the antibiotic were collected, concentrated and lyophilized to yield 38.6 g of crude GE23077 complex.

A fraction (28 g) of the crude preparation above described, was dissolved in 100 ml of 0.1M $(NH_4)_2SO_4$ buffer, and then was applied on top of a 46×7.5 cm chromatographic column containing silanised silica gel with particle size 70–230 mesh ASTM, (E. Merck; Darmstadt F. R. Germany) which was equilibrated with 0.1 M ammonium sulphate buffer (pH 7). The column was eluted at a flow rate of 60 ml/min using a medium pressure apparatus (Buchi Preparative LC-system B680-A). GE23077 complex was eluted by increasing stepwise the percentage of methanol in 0.1 M ammonium sulphate buffer (pH 7). All the eluted fractions were analyzed by HPLC and using the functional assay for RNA polymerase inhibition.

The working analytical HPLC method was performed on the apparatus HP mod. 1090 (Hewlett Pachard Co.), equipped with a column C18 Ultrasphere ODS (5 µm particle size, 250×4.6 mm; Beckmann. Co.). Phase A was a mixture of methanol:100 mM ammonium sulphate buffer, 5:95 (v/v). Phase B was a mixture of methanol:water, 2:8 (v/v,). A linear gradient starting from 50% to 80% of phase B was applied in 20 min. The flow rate was 1 ml/min and the elution monitored with UV-DAD detector at 230 nm.

Retention times observed with this method were: 14.4 min (factor A1 ), 16.5 min (factor B1), 19.4 min (factor A2), 21.3 min (factor B2).

The active fractions were pooled and dried under reduced pressure. The obtained solid residue, containing GE23077 complex and $(NH_4)_2SO_4$, was stirred at room temperature in methanol. The supernatant, containing the antibiotic, was removed and the solid residue was submitted to repeated cycles of washing with methanol. The pooled methanol extracts were concentrated under vacuum, dissolved in water and freeze dried, yielding 4.9 g of GE23077 complex. The complex was further purified by chromatography on 20 ml Supelclean LC-SAX silica based anionic exchange resin (Supelco Inc; Bellefonte, USA). A portion (500 mg) of the complex preparation as above described was dissolved in a water and was loaded on the resin, in the chloride salt form, equilibrated in water. After repeated washing with water, a 160 min linear gradient was applied from 0 to 1 mM HCl. The eluted fractions were analyzed by HPLC and those containing GE23077 complex were pooled and lyophilized, yielding 210 mg of purified GE23077 complex in the acid form, as a white powder.

EXAMPLE 3

Improved Method for Purification of GE23077 Complex

Four fermentation runs, as described in Example 1, were harvested and processed on S112 resin as described in Example 2. The solid residue eluted with acetone:water:n-butanol 8:1:1 (v/v) was dissolved in methanol and precipitated upon addition of ethyl ether, yielding 318 g of crude GE23077 complex.

A portion (294 g) of this material was dissolved in water and applied on top of a 11×96 cm column containing 9 l of HP20 polystyrenic resin (Mitsubishi Chemical Co.). The column was washed with 27 l of water and then eluted with acetone:water 5:95 (v/v). The fractions collected were analysed by HPLC and for RNA polymerase inhibition. The fractions containing the GE23077 complex were pooled and concentrated under reduced pressure. The solid residue was dissolved in methanol and precipitated upon addition of ethyl ether, yielding 55.2 g of antibiotic GE23077 complex, as solid residue.

25 g of this preparation were purified on a column containing 2.5 l of Q-sepharose Fast Flow resin (Pharmacia Fine Chemicals, AB), equilibrated with 50 mM sodium acetate pH 3.5 buffer. The column was eluted with the same buffer, and each fraction was analysed by TLC on RP-8 plates (E. Merck; F. R. Darmstadt, Germany), eluted with the same buffer. The fractions containing the GE23077 complex, were pooled and were desalted by adsorption on 1 l of HP-20 resin (Mitsubishi Chemical Co.), by washing with water and by eluting with water:acetone 9:1 (v/v). The pooled fractions, containing GE23077 complex, were concentrated to dryness and were resuspended in acetone. The solid residue was filtered yielding 6.2 g of purified GE23077 complex.

EXAMPLE 4

Isolation of Factors A1, A2, B1 and B2

210 mg of GE23077 complex, prepared as described in Example 2, were fractionated by repeated chromatographic runs of preparative HPLC on a 250×10 mm Supelcosil LC8 column, 5 µm. (Supelco Inc; Bellefonte, USA). 12 mg of complex dissolved in water were processed in each chromatographic run. The separation was performed by eluting at 4 ml/min flow rate with a 25 min linear gradient from 50% to 80% of phase B, followed by 5 min elution with 80% of phase B. Phase A was methanol:100 mM ammonium sulphate, pH 7 buffer, 5:95 (v/v), and Phase B was methanol:water 2:8 (v/v). UV detection was at 230 nm. The eluted fractions containing the individual GE23077 factors were collected and freeze dried. To remove the inorganic salts from the GE23077 factors, the solid residue was stirred at room temperature in methanol. The methanol supernatant was removed and the solid residue was submitted to repeated cycles of washing with methanol. The methanol layers, containing the antibiotic, were pooled and were concentrated to dryness under vacuum. The residue, dissolved in water, was then lyophilized, yielding 41 mg of factor A1, 36 mg of factor B1, 31 mg of factor A2 and 32 mg of factor B2.

What is claimed is:
1. Antibiotic GE23077 factor A1 having the following characteristics:
  A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 804 m/z;
  B) $^1$H-NMR spectrum recorded at 600 MHz in DMSO-d$_6$, exibiting the following signals (in ppm) referenced to the residual peak of DMSO set at 2.5 ppm as internal standard: the values marked with an asterisk are overlapping of two $^1$H signals:
    8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/ 3.49; 3.53,3.42/3.25; 2.50; 1.74; 1.70; 0.96; 0.94; 0.85;
  C) $^{13}$C-NMR spectrum, recorded at 150 MHz in DMSO-d$_6$, exibiting the following signals (in ppm) referenced to the residual peak of DMSO set at 39.5 ppm as internal; standard: the values marked with an asterisk are overlapping of two $^{13}$C signals:
    175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.51; 19.3; 19.2; 13.7; 12.3;
  D) Retention time: 14.16 min, determined by HPLC analysis under the following chromatographic conditions:
    Instrument: HP mod. 1090 DAD detector;
    Column: Beckmann ODS C18, 5 µm 250×4.6 mm;
    Elution: Isocratic 15% Phase B;
    Phase A: 2.5 g/l Ammonium formiate: 99:1 v/v Methanol;
    Phase B: 2.5 g/l Ammonium formiate: 30:70 v/v Methanol;
    Flow rate: 1.5 ml/min;
    Detector: UV 230 nm;
  and the pharmaceutically acceptable salts thereof.
2. Antibiotic GE23077 factor A2 having the following characteristics:
  A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 804 m/z;
  B) Retention time: 20.90 min, determined by HPLC analysis under the following chromatographic conditions:
    Instrument: HP mod. 1090 DAD detector;
    Column: Beckmann ODS C18, 5 µm 250×4.6 mm;
    Elution: Isocratic 15% Phase B;
    Phase A: 2.5 g/l Ammonium formiate: 99:1 v/v Methanol;
    Phase B: 2.5 g/l Ammonium formiate: 30:70 v/v Methanol;
    Flow rate: 1.5 ml/min;
    Detector: UV 230 nm;
  C) $^1$H-NMR spectrum, recorded after complete conversion of factor A2 into factor A1 was recorded at 600 MHz in DMSO-d$_6$ and exibits the following signals (in ppm) referenced to the residual peak of DMSO set at 2.5 ppm as internal standard: the values marked with an asterisk are overlapping of two $^1$H signals:
    8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/ 3.49; 3.53,3.42; 3.25; 2.50; 1.74; 1.70; 0.96; 0.94; 0.85;
  D) $^{13}$C-NMR spectrum, recorded after complete conversion of factor A2 into factor A1 was recorded at 150 MHz in DMSO-d$_6$ and exibits the following signals (in ppm) referenced to the residual peak of DMSO set at 39.5 ppm as internal standard: the values marked with an asterisk are overlapping of two $^{13}$C signals:
    175.6; 171.5; 171.3; 170.7; 170.2; 170.0; 170.0*; 169.6; 169.2; 168.8; 131.6; 1219.9; 74.0; 69.9; 69.1; 66.8; 63.1; 60.1; 58.5; 58.2; 57.3; 55.9; 54.3; 43.4; 39.7; 29.8; 19.9; 19.3; 19.2; 13.7; 12.3;
  and the pharmaceutically acceptable salts thereof.
3. Antibiotic GE23077 factor B1 having the following characteristics:
  A) Main FAB mass peak, obtained on a Finnigan TSQ700 triple quadrupole. mass spectrometer using a xenon atom gun, operating at 8 kV, 0.23 mA current, the sample being mixed with glycerol as ionization matrix, corresponding to (M–H)$^+$ at 806 m/z;
  B) $^1$H-NMR spectrum, recorded at 600 MHz in DMSO-d$_6$, exibiting the following signals (in ppm) referenced to the residual peak of DMSO set at 2.5 ppm as internal standard: the values marked with an asterisk are overlapping of two $^1$H signals;
9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84;

C) $^{13}$C-NMR spectrum, recorded at 150 MHz in DMSO-d$_6$, exibiting the following signals (in ppm) referenced to the residual peak of DMSO set at 39.5 ppm as internal standard: the values marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

D) Retention time: 16.56 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

and the pharmaceutically acceptable salts thereof.

4. Antibiotic GE23077 factor B2 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 806 m/z;

B) Retention time: 22.71 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

C) The $^1$H-NMR spectrum, recorded after complete conversion of factor B2 into factor B1 was recorded at 600 MHz in DMSO-d$_6$ and exibits the following signals (in ppm) referenced to the residual peak of DMSO set at 2.5 ppm as internal standard: the values marked with an asterisk are overlapping of two $^1$H signals:
9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84;

D) The $^{13}$C-NMR spectrum, recorded after complete conversion of factor B2 into factor B1 was recorded at 150 MHz in DMSO-d$_6$ and exibits the following signals (in ppm) referenced to the residual peak of DMSO set at 39.5 ppm as internal standard: the values, marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

and the pharmaceutically acceptable salts thereof.

5. A process for producing an antibiotic, wherein the antibiotic is selected from the group consisting of antibiotic GE23077 factor A1 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 804 m/z;

B) $^1$H-NMR spectrum recorded at 600 MHZ in DMSO-d$_6$, exibiting the following signals (in ppm) referenced to the residual peak of DMSO set at 2.5 ppm as internal standard: the values marked with an asterisk are overlapping of two $^1$H signals;:
8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/3.49; 3.53,3.42/3.25; 2.50; 1.74; 1.70; 0.96; 0.94; 0.85;

C) $^{13}$C-NMR spectrum, recorded at 150 MHZ in DMSO-d$_6$, exibiting the following signals (in ppm) referenced to the residual peak of DMSO set at 39.5 ppm as internal standard: the values marked with an asterisk are overlapping of two $^{13}$C signals:
175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.9; 19.3; 19.2; 13.7; 12.3;

D) Retention time: 14.16 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm, a pharmaceutically acceptable salt of antibiotic GE23077 factor A1, antibiotic GE23077 factor A2 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 804 m/z;

B) Retention time: 20.90 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5μl Ammonium formiate: 99:1 v/v Methanol;
Phase B: 2.5 g/l Ammonium formiate: 30:70 v/v Methanol;
Flow rate: 1.5 ml/min;
Detector: UV 230 nm;

C) $^1$H-NMR spectrum, recorded after complete conversion of factor A2 into factor A1 was recorded at 600 MHZ in DMSO-d$_6$ and exibits the following signals (in ppm) referenced to the residual peak of DMSO set at 2.5 ppm as internal standard: the values marked with an asterisk are overlapping of two $^1$H signals:
8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/ 3.49; 3.53,3.42/3.25; 2.50; 1.74; 1.70; 0.96; 0.94; 0.85;

D) $^{13}$C-NMR spectrum, recorded after complete conversion of factor A2 into factor A1 was recorded at 150 MHZ in DMSO-$d_6$ and exibits the following signals (in ppm) referenced to the residual peak of DMSO set at 39.5 ppm as internal standard: the values marked with an asterisk are overlapping of two $^{13}$C signals:
175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.9; 19.3; 19.2; 13.7; 12.3, a pharmaceutically acceptable salt of antibiotic GE23077 factor A2, antibiotic GE23077 factor B1 having the following characteristics:

A) Main FAB mass peak, obtained on a Finnigan TSQ700 triple quadrupole. mass spectrometer using a xenon atom gun, operating at 8 kV, 0.23 mA current, the sample being mixed with glycerol as ionization matrix, corresponding to (M–H)$^+$ at 806 m/z;

B) $^1$H-NMR spectrum, recorded at 600 MHZ in DMSO-$d_6$, exibiting the following signals (in ppm) referenced to the residual peak of DMSO set at 2.5 ppm as internal standard: the values marked with an asterisk are overlapping of two $^1$H signals:
9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84;

C) $^{13}$C-NMR spectrum, recorded at 150 MHZ in DMSO-$d_6$, exibiting the following signals (in ppm) referenced to the residual peak of DMSO set at 39.5 ppm as internal standard: the values marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

D) Retention time: 16.56 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm, a pharmaceutically acceptable salt of antibiotic GE23077 factor B1, antibiotic GE23077 factor B2 having the following characteristics;

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 806 m/z;

B) Retention time: 22.71 min, determined by HPLC analysis under the following, chromatographic conditions:
Instrument: HP mod. 1090 DAD detector;
Column: Beckmann ODS C18,5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

C) The $^1$H-NMR spectrum, recorded after complete conversion of factor B2 into factor B1 was recorded at 600 MHZ in DMSO-$d_6$ and exibits the following signals (in ppm) referenced to the residual peak of DMSO set at 2.5 ppm as internal standard: the values marked with an asterisk are overlapping of two $^1$H signals:
9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84;

D) The $^{13}$C-NMR spectrum, recorded after complete conversion of factor A2 into factor A1 was recorded at 150 MHZ in DMSO-$d_6$ and exibits the following signals (in ppm) referenced to the residual peak of DMSO set at 39.5 ppm. as internal standard: the values marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

and a pharmaceutically acceptable salt of antibiotic GE23077 factor B2, which comprises:
cultivating Actinomadura sp. DSMZ 13491 or a mutant thereof;
isolating the resulting antibiotic from the mycelium and or the culture broth;
purifying the isolated antibiotic; and
separating the antibiotic four factors A 1, A2, B 1 and B2 by chromatographic means.

6. An antibiotic GE23077 mixture of two or more factors selected from the group consisting of antibiotic GE23077 factor A1 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 804 m/z;

B) $^1$H-NMR spectrum recorded at 600 MHz in DMSO-$d_6$, exibiting the following signals (in ppm) referenced to the residual peak of DMSO set at 2.5 ppm as internal standard: the values marked with an asterisk are overlapping of two $^1$H signals:
8.94; 8.93; 8.93*; 8.04; 7.93; 7.88; 7.68; 7.33/7.27; 7.29; 6.34; 5.97; 5.79; 5.68: 5.00; 4.94; 4.82; 4.65; 4.47; 4.37; 4.31; 4.07; 4.05; 3.90; 3.88; 3.74; 3.59/ 3.49; 3.53,3.42/3.2:5; 2.50; 1.74; 1.70; 0.96; 0.94; 0.85;

C) $^{13}$C-NMR spectrum, recorded at 150 MHz in DMSO-$d_6$, exibiting the following signals (in ppm) referenced to the residual peak of DMSO set at 39.5 ppm as internal standard: the values marked with an asterisk are overlapping of two $^{13}$C signals:
175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.9; 119.3; 19.2; 13.7; 12.3;

D) Retention time: 14.16 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm, a pharmaceutically acceptable salt of antibiotic GE23077 factor A1, antibiotic GE23077 factor A2 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to $(M-H)^+$ at 804 m/z;

B) Retention time: 20.90 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

C) $^1$H-NMR spectrum, recorded after complete conversion of factor A2 into factor A1 was recorded at 600 MHz in DMSO-$d_6$ and exibits the following signals (in ppm) referenced to the residual peak of DMSO set at 2.5 ppm as internal standard: the values marked with an asterisk are overlapping of two $^1$H signals:
8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/3.49; 3.53,3.42/3.25; 2.50; 1.74; 1.70; 0.96; 0.94; 0.85;

D) $^{13}$C-NMR spectrum, recorded after complete conversion of factor A2 into factor A1 was recorded at 150 MHz in DMSO-$d_6$ and exibits the following signals (in ppm) referenced to the residual peak of DMSO set at 39.5 ppm as internal standard: the values marked with an asterisk are overlapping of two $^{13}$C signals:
175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.9; 19.3; 19.2; 13.7; 12.3, a pharmaceutically acceptable salt of antibiotic GE23077 factor A2, antibiotic GE23077 factor B1 having the following characteristics:

A) Main FAB mass peak, obtained on a Finnigan TSQ700 triple quadrupole. mass spectrometer using a xenon atom gun, operating at 8 kV, 0.23 mA current, the sample being mixed with glycerol as ionization matrix, corresponding to $(M-H)^+$ at 806 m/z;

B) $^1$H-NMR spectrum, recorded at 600 MHz in DMSO-$d_6$, exibiting the following signals (in ppm) referenced to the residual peak of DMSO set at 2.5 ppm as internal standard: the values marked with an asterisk are overlapping of two $^1$H signals:
9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84;

C) $^{13}$C-NMR spectrum, recorded at 150 MHz in DMSO-$d_6$, exibiting the following signals (in ppm) referenced to the residual peak of DMSO set at 39.5 ppm as internal standard: the values marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

D) Retention time: 16.56 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm, a pharmaceutically acceptable salt of antibiotic GE23077 factor B1, antibiotic GE23077 factor B2 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to $(M-H)^+$ at 806 m/z;

B) Retention time: 22.71 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

C) The $^1$H-NMR spectrum, recorded after complete conversion of factor B2 into factor B1 was recorded at 600 MHz in DMSO-$d_6$ and exibits the following signals (in rpm) referenced to the residual peak of DMSO set at 2.5 ppm as internal standard: the values marked with an asterisk are overlapping of two $^1$H signals:
9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84;

D) The $^{13}$C-NMR spectrum, recorded after complete conversion of factor B2 into factor B1was recorded at 150 MHz in DMSO-$d_6$ and exibits the following signals (in ppm) referenced to the residual peak of DMSO set at 39.5 ppm as internal standard: the values marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

and a pharmaceutically acceptable salt of antibiotic GE23077 factor B2 in any proportion.

7. The mixture according to claim 6 having the following characteristics:
   A) Ultraviolet absorption spectrum, recorded on a Perkin-Elmer spectrophotcmeter mod. Lambda 16, exhibits the following characteristics:

|  | λ$_{max}$ (nm) |
   |---|---|
   | H$_2$O:CH$_3$OH 1:1 | 204 |
   | KOH | 218; |

B) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 804 and 806 m/z;
   C) The aminoacid analysis of the acid hydrolysate showing the presence of valine, serine, threonine, isoserine, glycine and 2,3 diaminopropanoic acid;
   D) Infrared absorption spectrum, recorded in nujol mull with an IFS-48 Fourier Transform spectrophotometer, exhibiting the following absorption maxima ν (cm$^{-1}$): 3292; 3072; 2955; 2924 (nujol); 2853 (nujol); 1732; 1686; 1655; 1628; 1545; 1462; 1377; 1317; 1263; 1219; 1113; 1049; 978; 721;
   E) Retention times of the four GE23077 factors: 14.16 min (A1 ), 16.56 min (B1), 20.90 min (A2), 22.71 min (B2), determined by HPLC analysis under the following chromatographic conditions:
   Instrument: HP mod. 1090 DAD detector;
   Column: Beckmann ODS C18, 5 μm 250×4.6 mm;
   Elution: Isocratic 15% Phase B;
   Phase A: 2.5 g/l Ammonium formiate: 99:1 v/v Methanol;
   Phase B: 2.5 g/l Ammonium formiate: 30:70 v/v Methanol;
   Flow rate: 1.5 ml/min;
   Detector: UV 230 nm;
   F) The $^1$H-NMR spectrum, was recorded at 600 mHz in DMSO-d$_6$:
   9.00; 8.93; 6.34; 4.65; 4.47; 4.04; 3.99; 3.90; 3.88; 3.74; 3.53, 2.53; 1.95; 1.87; 1.71; 1.67; 0.96; 0.87; 0.85;
   G) R$_f$ value of 0.7, analyzed by TLC using silica gel plates Merck 5714 and developing in ethanol:n-butanol:water 2:2:1 (v/v);
   and the pharmaceutically acceptable salts thereof.

8. A process for producing an antibiotic according to claim 7, which comprises:
   cultivating Actinomadura sp. DSMZ 13491 or a mutant thereof;
   isolating the resulting antibiotic from the mycelium and/or the culture broth; and
   purifying the isolated antibiotic.

9. The process according to claim 8, wherein purifying is by a chromatographic technique.

10. The process according to claim 8, wherein cultivating is under aerobic conditions, in an aqueous nutrient medium containing an assimilable source of carbon, nitrogen and inorganic salts.

11. The process according to claim 10, further comprising pre-culturing the Actinomadura sp. DSMZ 13491 or the mutant thereof.

12. A pharmaceutical composition comprising at least one antibiotic selected from the group consisting of antibiotic GE23077 factor A1 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 804 m/z;
B) $^1$H-NMR spectrum recorded at 600 MHz in DMSO-d$_6$, exibiting the following signals (in ppm) referenced to the residual peak of DMSO set at 2.5 ppm as internal standard: the values marked with an asterisk are overlapping of two $^1$H signals:
   8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/3.49; 3.53,3.42/3.25; 2.50; 1.74; 1.70; 0.96; 0.94; 0.85;
C) $^{13}$C-NMR spectrum, recorded at 150 MHz in DMSO-d$_6$, exibiting the following signals (in ppm) referenced to the residual peak of DMSO set at 39.5 ppm as internal standard: the values marked with an asterisk are overlapping of two $^{13}$C signals:
   175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.9; 19.3; 19.2; 13.7; 12.3;
D) Retention time: 14.16 min, determined by HPLC analysis under the following chromatographic conditions:
   Instrument: HP mod. 1090 DAD detector;
   Column: Beckmann ODS C18, 5 μm 250×4.6 mm;
   Elution: Isocratic 15% Phase B;
   Phase A: 2.5 g/l Ammonium formiate: 99:1 v/v Methanol;
   Phase B: 2.5 g/l Ammonium formiate: 30:70 v/v Methanol;
   Flow rate: 1.5 ml/min;
   Detector: UV 230 nm;
a pharmaceutically acceptable salt of antibiotic GE23077 factor A1, antibiotic GE23077 factor A2 having the following characteristics:
A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M–H)$^+$ at 804 m/z;
B) Retention time: 20.90 min, determined by HPLC analysis under the following chromatographic conditions:
   Instrument: HP mod. 1090 DAD detector;
   Column: Beckmann ODS C18, 5 μm 250×4.6 mm;
   Elution: Isocratic 15% Phase B;
   Phase A: 2.5 g/l Ammonium formiate: 99:1 v/v Methanol;
   Phase B: 2.5 g/l Ammonium formiate: 30:70 v/v Methanol;
   Flow rate: 1.5 ml/min;
   Detector: UV 230 nm;
C) $^1$H-NMR spectrum, recorded after complete conversion of factor A2 into factor A1 was recorded at 600 MHz in DMSO-d$_6$ and exibits the following signals (in ppm) referenced to the residual peak of DMSO set at 2.5 ppm as internal standard: the values, marked with an asterisk are overlapping of two $^1$H signals:
   8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/3.49; 3.53,3.42/3.25; 2.50; 1.74; 1.70; 0.96; 0.94; 0.85;

D) $^{13}$C-NMR spectrum, recorded after complete conversion of factor A2 into factor A1 was recorded at 150 MHz in DMSO-d$_6$ and exibits the following signals (in ppm) referenced to the residual peak of DMSO set at 39.5 ppm as internal standard: the values marked with an asterisk are overlapping of two $^{13}$C signals:
175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.9; 19.3; 19.2; 13.7; 12.3;

a pharmaceutically acceptable salt of antibiotic GE23077 factor A2, antibiotic GE23077 factor B1 having the following characteristics:

A) Main FAB mass peak, obtained on a Finnigan TSQ700 triple quadrupole. mass spectrometer using a xenon atom gun, operating at 8 kV, 0.23 mA current, the sample being mixed with glycerol as ionization matrix, corresponding to (M−H)$^+$ at 806 m/z;

B) $^1$H-NMR spectrum, recorded at 600 MHz in DMSO-d$_6$, exibiting the following signals (in ppm) referenced to the residual peak of DMSO set at 2.5 ppm as internal standard: the values marked with an asterisk are overlapping of two $^1$H signals:
9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84;

C) $^{13}$C-NMR spectrum, recorded at 150 MHz in DMSO-d$_6$, exibiting the following signals (in ppm) referenced to the residual peak of DMSO set at 39.5 ppm as internal standard: the values marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

D) Retention time: 16.56 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

a pharmaceutically acceptable salt of antibiotic GE23077 factor B1, antibiotic GE23077 factor B2 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M−H)$^+$ at 806 m/z;

B) Retention time: 22.71 min, determined by HPLC analysis under the following chromatographic conditions:
Instrument: HP mod. 1090 DAD detector;
Column: Beckmann ODS C18, 5 μm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

C) The $^1$H-NMR spectrum, recorded after complete conversion of factor B2 into factor B1 was recorded at 600 MHz in DMSO-d$_6$ and exibits the following signals (in ppm) referenced to the residual peak of DMSO set at 2.5 ppm as internal standard: the values marked with an asterisk are overlapping of two $^1$H signals:
9.00; 8.99; 8.94; 8.02; 7.93; 7.88; 7.82; 7.32/7.26; 7.30; 5.90; 5.81; 5.66; 4.99; 41.96; 4.79; 4.65; 4.47; 4.31; 4.31; 4.07; 4.05; 3.88; 3.88*; 3.74; 3.57/3.37; 3.53; 3.47/3.23; 2.69; 1.95; 1.95*; 0.95; 0.94; 0.85; 0.84;

D) The $^{13}$C-NMR spectrum, recorded after complete conversion of factor B2 into factor B1 was recorded at 150 MHz in DMSO-d$_6$ and exibits the following signals (in ppm) referenced to the residual peak of DMSO set at 39.5 ppm as internal standard: the values marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

and a pharmaceutically acceptable salt of antibiotic GE23077 factor B2.

13. The pharmaceutical composition according to claim 12, comprising a pharmaceutically acceptable carrier.

14. The pharmaceutical composition according to claim 12, comprising another antimicrobial agent selected from a penicillin, a cephalosporin, an aminoglycoside and a glycopeptide.

15. The process according to claim 5, wherein cultivating is under aerobic conditions, in an aqueous nutrient medium containing an assimilable source of carbon, nitrogen and inorganic salts.

16. The process according to claim 15, further comprising pre-culturing the Actinomadura sp. DSMZ 13491 or the mutant thereof.

17. A method of treating a bacterial infection comprising administering to a patient in need thereof an effective amount of at least one antibiotic selected from the group consisting of antibiotic GE23077 factor A1 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to (M−H)$^+$ at 804 m/z;

B) $^1$H-NMR spectrum recorded at 600 MHz in DMSO-d$_6$, exibiting the following signals (in ppm) referenced to the residual peak of DMSO set at 2.5 ppm as internal standard: the values marked with an asterisk are overlapping of two $^1$H signals:
8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/3.49; 3.53,3.42/3.25; 2.50; 1.74; 1.70; 0.96; 0.94; 0.85;

C) $^{13}$C-NMR spectrum, recorded at 150 MHz in DMSO-d$_6$, exibiting the following signals (in ppm) referenced to the residual peak of DMSO set at 39.5 ppm as internal standard: the values marked with an asterisk are overlapping of two $^{13}$C signals:
175.6; 171.5; 171.3; 170.7; 170.2; 170.0; 170.0*; 169.6; 169.2; 168.8; 131.6; 12.9.9; 74.0; 69.9; 69.1; 66.8; 63.1; 60.1; 58.5; 58.2; 57.3; 55.9; 54.3; 43.4; 39.7; 29.8; 19.9; 19.3; 19.2; 13.7; 12.3;

D) Retention time: 14.16 min, determined by HPLC analysis under the following chromatographic conditions:

Instrument: HP mod. 1090 DAD detector;
Column: Beckmann ODS C18, 5 µm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

a pharmaceutically acceptable salt of antibiotic GE23077 factor A1, antibiotic GE23077 factor A2 having the following characteristics:

A) Main FAB mass peak, obtained on a Finnigan TSQ700 triple quadrupole mass spectrometer using a xenon atom gun, operating at 8 kV, 0.23 mA current, the sample being mixed with glycerol as ionization matrix, corresponding to $(M–H)^+$ at 804 m/z;

B) Retention time: 20.90 min, determined by HPLC analysis under the following chromatographic conditions:
Instrument: HP mod. 1090 DAD detector;
Column: Beckmann ODS C18, 5 µm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

C) $^1$H-NMR spectrum, recorded after complete conversion of factor A2 into factor A1 was recorded at 600 MHz in DMSO-$d_6$ and exibits the following signals (in ppm) referenced to the residual peak of DMSO set at 2.5 ppm as internal standard: the values marked with an asterisk are overlapping of two $^1$H signals:
8.94; 8.93; 8.93*; 8.04; 7.93; 7.88; 7.68; 7.33/7.27; 7.29; 6.34; 5.97; 5.79; 5.68; 5.00; 4.94; 4.82; 4.65; 4.47; 4.37; 4.31; 4.07; 4.05; 3.90; 3.88; 3.74; 3.59/3.49; 3.53,3.42/3.25; 2.50; 1.74; 1.70; 0.96; 0.94; 0.85;

D) $^{13}$C-NMR spectrum, recorded after complete conversion of factor A2 into factor A1 was recorded at 150 MHz in DMSO-$d_6$ and exibits the following signals (in ppm) referenced to the residual peak of DMSO set at 39.5 ppm as internal standard: the values marked with an asterisk are overlapping of two $^{13}$C signals:
175.6; 171.5; 171.3; 170.7; 170.2; 170.0; 170.0*; 169.6; 169.2; 168.8; 131.6; 129.9; 74.0; 69.9; 69.1; 66.8; 63.1; 60.1; 58.5; 58.2; 57.3; 55.9; 54.3; 43.4; 39.7; 29.8; 19.9; 15.3; 19.2; 13.7; 12.3;

a pharmaceutically acceptable salt of antibiotic GE23077 factor A2, antibiotic GE23077 factor B1 having the following characteristics:

A) Main FAB mass peak, obtained on a Finnigan TSQ700 triple quadrupole. mass spectrometer using a xenon atom gun, operating at 8 kV, 0.23 mA current, the sample being mixed with glycerol as ionization matrix, corresponding to $(M–H)^+$ at 806 m/z;

B) $^1$H-NMR spectrum, recorded at 600 MHz in DMSO-$d_6$, exibiting the following signals (in ppm) referenced to the residual peak of DMSO set at 2.5 ppm as internal standard: the values marked with an asterisk are overlapping of two $^1$H signals:
9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84;

C) $^{13}$C-NMR spectrum, recorded at 150 MHz in DMSO-$d_6$, exibiting the following signals (in ppm) referenced to the residual peak of DMSO set at 39.5 ppm as internal standard: the values marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

D) Retention time: 16.56 min, determined by HPLC analysis under the following chromatographic conditions:
Instrument: HP mod. 1090 DAD detector;
Column: Beckmann ODS C18, 5 µm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

a pharmaceutically acceptable salt of antibiotic GE23077 factor B1, antibiotic GE23077 factor B2 having the following characteristics:

A) Main FAB mass peak, obtained on a Finnigan TSQ700 triple quadrupole miss spectrometer using a xenon atom gun, operating at 8 kV, 0.23 mA current, the sample being mixed with glycerol as ionization matrix, corresponding to $(M–H)^+$ at 806 m/z;

B) Retention time: 22.71 min, determined by HPLC analysis under the following chromatographic conditions:
Instrument: HP mod. 1090 DAD detector;
Column: Beckmann ODS C18, 5 µm 250×4.6 mm;
Elution: Isocratic 15% Phase B;
Phase A: 2.5 g/l Ammonium formiate: 99:1 v/v Methanol;
Phase B: 2.5 g/l Ammonium formiate: 30:70 v/v Methanol;
Flow rate: 1.5 ml/min;
Detector: UV 230 nm;

C) The $^1$H-NMR spectrum, recorded after complete conversion of factor B2 into factor B1 was recorded at 600 MHz in DMSO-$d_6$ and exibits the following signals (in ppm) referenced to the residual peak of DMSO set at 2.5 ppm as internal standard: the values marked with an asterisk are overlapping of two $^1$H signals:
9.00; 8.99; 8.94; 8.02; 7.93; 7.88; 7.82; 7.32/7.26; 7.30; 5.90; 5.81; 5.66; 4.99; 4.96; 4.79; 4.65; 4.47; 4.31; 4.31; 4.07; 4.05; 3.88; 3.88*; 3.74; 3.57/3.37; 3.53; 3.47/3.23; 2.49; 1.95; 1.95*; 0.95; 0.94; 0.85; 0.84;

D) The $^{13}$C-NMR spectrum, recorded after complete conversion of factor B2 into factor B1 was recorded at 150 MHz in DMSO-$d_6$ and exibits the following signals (in ppm) referenced to the residual peak of DMSO set at 39.5 ppm as internal standard: the values marked with an asterisk are overlapping of two $^{13}$C signals:
175.5; 172.3; 171.4; 171.3; 170.7; 170.2; 169.9; 169.9*; 169.5; 169.0; 73.9; 70.0; 69.0; 66.8; 63.1; 60.0; 58.4; 58.3; 57.3; 55.9; 54.5; 44.5; 43.5; 39.4; 29.8; 25.4; 22.3; 19.9; 19.2; 19.2;

and a pharmaceutically acceptable salt of antibiotic GE23077 factor B2.

* * * * *